United States Patent
Battistini et al.

(12)

(10) Patent No.: US 6,245,742 B1
(45) Date of Patent: Jun. 12, 2001

(54) PEPTIDE ANTAGONISTS OF CELLULAR MITOGENESIS AND MOTOGENESIS AND THEIR THERAPEUTIC USE

(75) Inventors: Carlo Battistini, Novate Milanese; Patrizia Giordano, Cuneo; Sabrina De Rosa, Cava dei Tirreni; Fabio Corradi, Milan; Paolo Comoglio; Alberto Bardelli, both of Turin, all of (IT)

(73) Assignee: Pharmacia & Upjohn S.p.A., Milan (IT)

( * ) Notice: Subject to any disclaimer, the term of this patent is extended or adjusted under 35 U.S.C. 154(b) by 0 days.

(21) Appl. No.: 08/930,616

(22) PCT Filed: Feb. 10, 1997

(86) PCT No.: PCT/EP97/00595

§ 371 Date: Oct. 15, 1997

§ 102(e) Date: Oct. 15, 1997

(87) PCT Pub. No.: WO97/30079

PCT Pub. Date: Aug. 21, 1997

(30) Foreign Application Priority Data

Feb. 15, 1996 (GB) .................................................. 9603227

(51) Int. Cl.[7] .................................................. A61K 38/00
(52) U.S. Cl. .................................. 514/18; 514/12; 514/13; 514/14; 514/15; 514/16; 514/17; 530/324; 530/325; 530/326; 530/327; 530/328; 530/329; 530/330; 530/331; 530/334; 530/345
(58) Field of Search .................................. 514/18, 12–17; 530/324–331 R, 334, 345

(56) References Cited

U.S. PATENT DOCUMENTS

| | | | |
|---|---|---|---|
| 5,594,105 | 1/1997 | Comoglio et al. | ................... 530/326 |
| 5,739,278 | * 4/1998 | Daum et al. | ..................... 530/328 |
| 5,801,149 | * 9/1998 | Shoelson | ................................ 514/18 |
| 5,912,183 | * 6/1999 | Comoglio et al. | ................... 436/501 |

FOREIGN PATENT DOCUMENTS

9501376 * 12/1995 (WO).

OTHER PUBLICATIONS

C. Battistini et al, Abstract No. 204, "Minimal Structural Requirements of Peptide Substrates for inhibition of the HGF Receptor/BRB2–SH2 Recognition", presented at the Keystone Simposia held in Keystone, Colorado on Mar. 31–Apr. 6, 1997.

N. Schiering et al, Abstract No. 231, "The Crystal Structure of the Complex Between the GRB2–SH2 Domain and the Tetrapeptide pYVNV", presented at the Keystone Simposia held in Keystone, Colorado on Mar. 31–Apr. 6, 1997.

DN 123: 257331, Otaka et al., *Pept. Chem.*, (1995) Volume Date 1994, 32$^{nd}$, 9–12 (Abstract).*

* cited by examiner

*Primary Examiner*—Dwayne C. Jones
*Assistant Examiner*—C. Delacroix-Muirheid
(74) *Attorney, Agent, or Firm*—Oblon, Spivak, McClelland, Maier & Neustadt, P.C.

(57) ABSTRACT

The present invention relates to peptides and peptidomimetic compounds and pharmaceutical compositions containing them as useful pharmacological agents in the control or treatment of proliferative diseases such as cancer, against tumor growing and/or tumoral metastasis, and psoriasis and in the control or treatment of inflammatory, allergic, autoimmune, viral, and cardiovascular diseases. These new compounds have the unique property to inhibit the recognition of several phosphotyrosine containing motifs within all the cellular receptors and cytosolic transducers by a wide spectrum of SH2 domains contained in cytosolic transducers and other effector proteins laying along different pathways of the signal transduction process and with a particularly high affinity for the SH2 domain of the adaptor transducer Grb2, a key element along the pathway to mitogenesis and motogenesis, this last activity leading to invasiveness and to metastasis. The invention also relates to methods for production of the compounds and methods of treatment employing the compounds.

33 Claims, 3 Drawing Sheets

FIG.2A
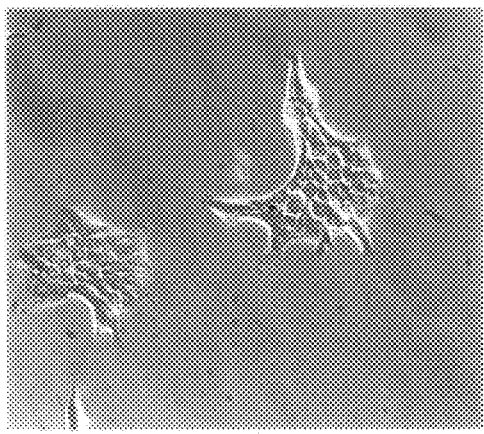
CONTROL
FIG.2B
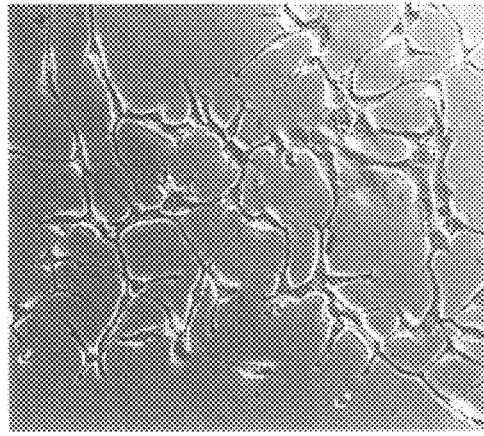
FCE 29606
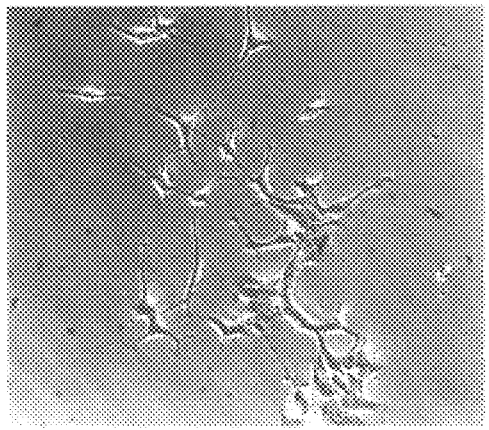
HGF
FIG.2C
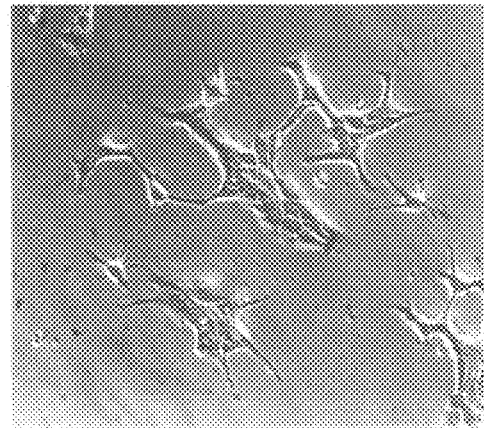
FCE 29408
FIG.2D

FCE 29408

FCE 29606

PEPTIDE ANTAGONISTS OF CELLULAR MITOGENESIS AND MOTOGENESIS AND THEIR THERAPEUTIC USE

This application is a 371 of PCT/EP97/00595 filed Feb. 10, 1997.

FIELD OF THE INVENTION

The present invention relates to novel compounds and pharmaceutical compositions containing the compounds as useful pharmacological agents in the control or treatment of proliferative diseases such as cancer, against tumor growing and/or tumoral metastasis, and psoriasis and in the control or treatment of inflammatory, allergic, autoimmune, viral, and cardiovascular diseases. These new compounds have the unique property to inhibit the recognition of several phosphotyrosine containing motifs within all the cellular receptors and cytosolic transducers by a wide spectrum of SH2 domains contained in cytosolic transducers and other effector proteins laying along different pathways of the signal transduction process and with a particularly high affinity for the SH2 domain of the adaptor transducer Grb2, a key element along the pathway to mitogenesis and motogenesis, this last activity leading to invasiveness and to metastasis. The invention also relates to methods for production of the compounds and methods of treatment employing the compounds.

BACKGROUND OF THE INVENTION

The cytosolic signal transduction pathways from the receptor to the nucleus follow the interactions of extracellular growth factors with their receptors embedded in the cell membrane and involve an intracellular complex chain of biochemical events, still partially unknown, that leads signals to the nucleus in order to stimulate the proper biological response. In the signal transduction eliciting mitogenesis, an activated receptor transmits in some way a signal to cytosolic or membrane anchored proteins like one appearing to have a pivotal role in the mechanism, namely the $p21^{ras}$ protein. In turn these proteins are able to transduce further the signal in a multistep way to the nucleus. There are several human tumors in which activated ras proto-oncogenes have been detected. The frequency of activation may be very high; for example, activated ras gene occur in 30% of all human haemopoietic neoplasms and more than 90% of tumors of the exocrine pancreas. In general protooncogenes lead to normal proteins, like tyrosine kinase receptors and transducers, heavily involved in the cell signalling. Several oncogenes are mutated or overexpressed forms or chimeric genes from chromosomal translocation, coding for proteins that act in the signal transduction mechanism, and giving rise to constitutively activated signalling proteins that cause an uncontrolled cell growth resulting in tumor progression. Intracellular signalling is being elucidated more and more in the nature of its components and in their role, disclosing a more and more attractive set of possible targets for conceptually new approaches to antitumoral therapy. The signalling from the activated receptor to the nucleus seems to involve several proteins interacting along maybe redundant pathways, more or less interconnected. Among the main types of molecular events involved, some are of particular relevance: 1) protein tyrosine phosphorylation (kinase activity); 2) recognition (physical association between specific protein domains); 3) protein serine/threonine phosphorylation (kinase activity); 4) dephosphorylation by specific enzymes (phosphatases), because both tyrosine and serine/threonine phosphorylation are also regulated through the reversing effect. These events can occur more than once in the net of the signal transduction pathways. Among these main interactions, an appealing target for a therapeutical approach is the recognition of the phosphorylated tyrosine domain with the "cytosolic transducers".

As first step the growth factor (for example EGF, FGF, PDGF, HGF, . . . ) activates its receptor, a protein spanning the cell membrane, by interacting with it and causing mutual proximity of the receptor molecules. Indeed the receptor molecules are brought close to each other allowing inside the cell a reciprocal phosphorylation at the level of intracellular domains operated by the kinase domain of one molecule on several tyrosine residues of the cytosolic portion of the adjacent molecule, or undergo a phosphorylation by an associated tyrosine kinase. Once the cytosolic regions of the receptor have several sites phosphorylated at tyrosine a molecular recognition can occur between these phosphorylated sites and proper domains of several other proteins.

These proteins are "cytosolic transducers"; indeed they provide to continue the pathway of the signal transduction linking the ligand binding to the receptor to the regulation of nuclear factors controlling the transcription of genes and hence ultimately to the generation of biological responses such as cell proliferation (J. Schlessinger and A. Ullrich, Neuron, 1992, 9, 383; J. Schlessinger, Trends Biochem. Sci., 1993, 18, 273.). They all have a domain named SH2 (Src Homology 2) with a high degree of homology in the primary structure and even more conserved in the tertiary structure. These short (approximately 100 amino acids) SH2 domains are non-catalytic regions that are responsible for the binding with phosphotyrosine containing proteic segments (T. Pawson and G. D. Gish, Cell, 1992, 71, 359.). The interest and studies on structure and role of these SH2 domains have raised sharply in the last years. An analogous interest has been elicited by SH3 domains (Src Homology 3), less caracterized in function but often accompaning the presence of SH2 domains in the cytosolic transducers. SH3 domains also are non catalytic regions with high homology and that seem to have affinity for glycine-proline rich domains. Both SH2 and SH3 regions are thought to have a pivotal role in the signal transduction for intramolecular recognition. One group of SH2 containing proteins includes proteins having an intrinsic enzymatic activity, hence endowed with catalytic domains (kinase domains or others) besides the SH2 domain, like the proteins Src, Abl, Syc, PTP1C, PLCg, GAP, vav. Another group comprises SH2 containing proteins devoid of any known catalytic domain, that seem to have the function of adaptors recruiting to the receptor other proteins endowed with catalytic properties. For example this is the case of p85 that provides a link between the activated (phosphorylated) receptor and the activity of phosphatidyl-inositol-3'-kinase (PI3K). Another relevant example of adaptor is Grb2 (growth factor receptor binding protein 2) that links the phosphorylated receptor (EGF-R, PDGF-R, HGF-R, . . . ) to a protein that has a guanine nucleotide exchange activity on $p21^{ras}$, activating a system like ras, directly related to mitogenesis. Other SH2-containing adaptors seem to be Shc, Crk, Nck. Some of the mentioned transducers, particularly Grb2, and the related binding site on receptors like HGFR, articularly the site comprising Tyr 1356 of HGF receptor, seem to be strongly related to cell motogenesis, to invasiveness, and finally to metastasis. The peculiar SH2 domain is able to recognize the phosphorylated tyrosines and the flanking sequences of the receptors. or some other intermediate proteins. The core element of the rather conserved structure is an antiparallel β-sheet that is sandwiched between two α-helices and a small β-sheet protruding out from the sandwich; this structure has been clarified by X-ray and NMR studies (G. Waksman, D. Kominos, S. C. Robertson, N. Pant, D. Baltimore, R. B. Birge, D. Cowburn, H. Hanafusa, B. J. Mayer, M. Overduin, M. D. Resh, C. B. Rios, L. Silverman and J. Kuriyan, *Nature,* 1992, 358, 646; G. Waksman, S. E. Shoelson, N. Pant, D. Cowburn and J. Kuriyan, *Cell,* 1993, 72, 779; M. Overduin, C. B. Rios, B. J. Mayer, D. Baltimore and D. Cowburn, *Cell,* 1992, 70, 697) also in the complex form with binding peptides, like in the case of the Src SH2 domain. Anyway loops and turns differ among the several transducers, and can be related to the recognition specificity. Analyzing the phosphorylated receptor interactions with the cytosolic transducers, we can see: 1) that each of the several receptors links with almost the same proteins and 2) that each of them can do it with a certain degree of regiospecificity, namely for several receptors different SH2 containing transducers bind different phosphotyrosine residues of the receptor cytosolic domain (J. A. Escobedo, D. R. Kaplan, W. M. Kavanaugh, C. W. Turck and L. T. Williams, *Mol. Cell. Biol.,* 1991, 11, 1125; A. Kashishian, A. Kazlauskas and J. A. Cooper, *EMBO J.,* 1992, 11, 1373; C.-H. Heldin, *EMBO J.,* 1992, 11, 4251 ). The high specificity arises from the sequence surrounding the phosphotyrosine, particularly downstream, different recognition motifs occurring for each transducer (W. J. Fantl, J. A. Escobedo, G. A. Martin, C. W. Turck, M. del Rosario, F. McCormick and L. T. Williams, *Cell,* 1992, 69, 413 ). A phosphopeptide library has been done to analyze the sequence specificity of several cytosolic transducers and determining the relative consensus sequences (Z. Songyang, S. E. Shoelson, M. Chaudhuri, G. Gish, T. Pawson, W. G. Haser, F. King, T. Roberts, S. Ratnofsky, R. J. Lechleider, B. G. Neel, R. B. Birge, J. E. Fajardo, M. M. Chou, H. Hanafusa, B. Schaffhausen and L. C. Cantley, *Cell,* 1993, 72, 767).

Indeed for the receptor of Hepatocyte Growth Factor (HGF), that is a powerful mitogen for hepatocytes in primary cultures and the major mediator of liver regeneration in vivo (P. M. Comoglio, in *Hepatocyte Growth Factor-Scatter Factor* (HGF-SF) and the c-Met receptor. I. D. Goldberg and E. M. Rosen Eds. (Basel), Switzerland: Birkauser Verlag, 1993, 131–165 ), the interactions of all the cytosolic transducers seem to be concentrated on a same "supersite" involving two close phosphotyrosine residues (C. Ponzetto, A. Bardelli, Z. Zhen, P. dalla Zonca, F. Maina, S. Giordano, A. Graziani, G. Panayotou and P. M. Comoglio, *Cell,* 1994, 77, 261).

The growth factor receptor-bound protein 2 (Grb2) is a relatively small adapter simply constituted by a SH2 domain flanked by two SH3 domains and Grb2 forms a complex in vivo with another protein, SoS, through the binding of its SH3 domains with a 31 aminoacid proline-rich stretch located in the C-terminal domain of SoS , that in turn is able to interact with the ras system. Grb2, also in the complex form with SoS, is able to associate through its SH2 domain with specific tyrosine-phosphorylated sites of different receptors or transducers. Also the phosphorylated form of the cytosolic protein Shc can bind the SH2 domain of Grb2 (S. E. Egan, B. W. Giddings, M. W. Brooks, L. Buday, A. M. Sizeland and R. A. Weinberg, *Nature,* 1993, 363, 45 ). The connection of the Grb2/SoS complex with the Ras system is proved for HGFR (A. Graziani, D. Gramaglia, P. dalla Zonca and P. M. Comoglio, *J. Biol. Chem.,* 1993, 268, 9165) and is largely supported by parallel cases with other receptors (EGFR , IRS-1) and in different biological species (J. Schlessinger and A. Ullrich, *Neuron,* 1992, 9, 383 ; J. Schlessinger, *Trends Biochem. Sci.,* 1993, 18, 273 ; P. Polakis and F. McCormick, *J. Biol. Chem.,* 1993, 268, 9157). The protein SoS is also known as "exchanger", Guanine nucleotide Dissociation Stimulator (GDS), and in its active form, complexed with Grb2 , is able to promote the fast GDP release from the inactive Ras-GDP complex (C. F. Albright, B. W. Giddings, J. Liu, M. Vito and R. A. Weinberg, *EMBO J.,* 1993, 12, 339). Hence $p_{21}^{Ras}$ can rapidly take GTP to form the active Ras-GTP, that in turn can act on the effectors of the Ras system transmitting the signal downstream to the nucleus (through the MAP kinase cascade). The membrane anchored complex Ras-GTP is the active form that acts on the effectors to transmit the mitogenesis signal to the nucleus. Its level is increased by the exchanger (GDS or SoS) activity and decreased by the GAP (GTPase activating protein) activity. Both these regulating enzymes are affected by growth factor receptor stimulation and furthermore their activity may depend from other regulatory factors. The two regulating enzymes, GDS and GAP, can have a different impact on Ras system in different cell type. Indeed, the mentioned regulations of the Ras system require a mature form of $p_{21}^{ras}$ suitable to be anchored to the membrane (C. J. Marshall, *Science,* 1993, 259, 1865). In these cases cell culture results have confirmed that the Ras system is a valuable target for preventing relevant oncogenic transformations (J. B. Gibbs, A. Oliff, and N. E. Kohl, *Cell,* 1994, 77, 175). Continuing on the signal transduction pathway (downstream of Ras), the active form of the Ras system, namely Ras GTP, interacts with the N-terminus of its own effector, recently identified as the serine/threonine kinase Raf , thus initiating a cascade of phosphorylation by the "mitogen-activated protein kinases" (MAPs). Indeed, Raf provides the direct phosphorylation and hence activation of MAP kinase kinase (MEK) that in turn activates MAPK, leading to the activation of transcription (transcription factor AP1) in the nucleus (M. S. Marshall, *Trends Biochem. Sci.,* 1993, 18, 250).

SUMMARY OF THE INVENTION

It is known that a peptide containing the motif $Y^PVNV$ within a longer sequence is able to inhibit the binding between the cytosolic transducers Shc or Grb2 or p85 and the activated (phosphorylated) HGF receptor (international patent application PCT/EP94/01943) . What we have now found is the following.

1) Within peptides starting from phosphorylated tyrosine, shortening the downstream sequence from the carboxyterminal end ,i.e. from a heptapeptide to a tetrapeptide the affinity for the transducer Grb2 unexpectedly increases and so the potency of inhibition of Grb2-HGFreceptor complex formation. Indeed this is an unexpected result because it is known from the literature related to SH2 recognition that the affinity of phosphopeptides decreases (even 60 times) with the decrease in length (for example from 12 to 5 amino acids) (G. B. Cohen et al., *Cell,* 1995, 80, 237 S. E. Shoelson et al., *EMBO J.,* 1993, 12, 795 ; E. Piccione et al., *Biochemistry,* 1993, 32, 3197), and in one case it is claimed that affinity requires at least a 5 amino acid length (W. J. Fantl et al., *Cell,* 1992, 69, 413).

2) Acylation of the a amino group of the phosphorylated tyrosine largely increases said activity. This acyl group can be a formyl , acetyl , propionyl or a more complex one, like for example an aminoacyl group or biotinyl-6-aminohexanoyl, or myristoyl, or octanoyl, or cyclohexylacetyl group, the last ones providing lipophilic anchor for improvement in cell penetration. To our knowledge in the literature almost all the phosphopeptides used in SH2 recognitions bear a free amino group at the N-terminus.

3) Said peptides are able to bind with high affinity and block Grb2 and several other transducers also, like Shc, p85, Src, GAP, PLCg, Zap70, Syc, Stat, preventing their coupling through their SH2 domains with whatever tyrosine phosphorylated receptor like for example HGF-R, PDGF-R, EGF-R, their truncated or mutated forms maintaining the cytoplasmic domain like erbB2, Tpr-MET and other members of the MET family like SEA and RON, IRS-1, tyrosine phosphorylated transducers or adaptors like bcr-Abl, Shc, Src, Syc, Stat. This unexpected peculiarity of these peptides is totally unprecedented, since other sequences have shown to be highly specific.

4) Totally unexpected was also the finding that even peptides shorter than the tetrapeptide motif, containing phosphotyrosine or mimetic analogues such as paraphosphonomethylphenylalanine, paraphosphonodifluorome thylphenylalanine, kept their activity in inhibiting the Grb2-SH2 binding with phosphorylated HGF receptor. It is absolutely unprecedented that a phosphopeptide as short as a tripeptide has a high affinity for SH2 recognitions. It is known for other sequences that phosphonomethylphenylalanyl derivatives are phosphatase resistant but usually much weaker than the corresponding phosphate analogues (6–10 fold) (S. M. Domchek et al., *Biochemistry*, 1992, 31, 9865); unexpectedly we found that phosphonomethylphenylalanyl analogues of our specific peptides are about equipotent as the parent phosphate for the inhibitition of Grb2-SH2 recognition. 5) Totally unexpected was also the finding that these peptides in the tyrosine-phosphorylated form or their mimetic analogues where the phosphotyrosine is substituted by para-phosphonomethylphenylalanine or para-phosphonodifluoromethylphenylalanine, are strong inhibitors of cell motility and are useful as antimetastatic agents besides as antitumoral agents.

Though not wishing to be bound by theory, this inhibition is probably the result of competitive inhibition wherein the phosphopeptide or its mimetic competes with the phosphorylated receptor or the phosphorylated transducer for the same binding site on the SH2 domain. Inhibition of this binding can effectively uncouple the TK receptor or a phosphorylated transducer from the signal transduction pathway utilized by the effector protein. Since it is well known in the field that the main drawback of this strategy is the strong possibility that this block point can be bypassed by the redundancy of the signal transduction pathways, the unprecedented ability of the compounds of this invention to inhibit several type of SH2 recognitions has to be considered a key factor for the efficacy in lowering the level of a disregulated signal transduction network.

Object of the present invention are therefore small molecule compounds able to interfere with the association of phosphotyrosine containing receptors or trasducers with the SH2 domains of other membrane-anchored or cytosolic transducers crucial for growth and motility/scattering signals and hence able to reduce the level of uncontrolled proliferation as found in tumors and psoriasis and capable to inhibit cell invasiveness much involved in metastasis.

The new compounds of the invention have been shown to inhibit particularly the binding of Grb2 trasducer to the phosphotyrosine docking site of HGF receptor other growth factor receptors (like EGFR, PDGFR, erbB2/neu, FGFR) and other tyrosine-phosphorylated transducers (like Src, bcr-abl, Stat, IRS-1). Nevertheless said compounds also inhibit the association of the phosphotyrosine docking site containing proteins with other SH2 containing transducers (like p85-PI3K, PLCg , Src, Shc, Stat, Zap70, Abl, Syc, PTPlC ) with different potency.

DETAILED DESCRIPTION OF THE INVENTION

The invention in one preferred aspect comprises peptide and peptidomimetic compounds in salt or nonsalt form having the formula

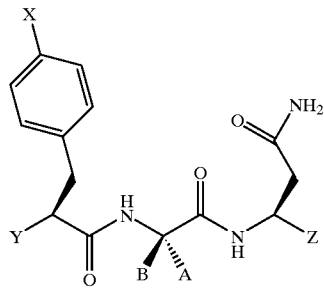

wherein Y is H— or R—C(=O)NH— where R can be H—, $CH_3$—, or low alkyl, or a long chain alkyl, linear branched or cyclic, or N-substituted amino acidic or peptidic residues, preferably , R—C(=O)—Gly—, R—C(=O)—Thr—, R—C(=O)—Ala—Thr— where R is defined as above, and longer N-substituted peptidic residues containing the above motif; X is —$OPO_3H_2$, or its mimics that can be preferably selected from, but not limited to, the following groups: —$CH_2PO_3H_2$, —$CF_2PO_3H_2$, —$CHFPO_3H_2$, —$CH_2SO_3H$, —$CF_2SO_3H$, —$CHFSO_3H$, —$SPO_3H_2$, —$OPSO_2H_2$, —$SPSO_2H_2$, —$OPS_2OH_2$, —OP $(CH_3)O_2H$, —SP $(CH_3)O_2H$, —OP $(CH_3)$ SOH, —$OP(CF_3)O_2H$, —$OP(CHF_2)O_2H$, —$SP(CF_3)O_2H$, —$SP(CHF_2)O_2H$, or their low alkyl esters; A is low alkyl, preferably $CH_3$—, $CH_3CH_2$—, $(CH_3)_2$ CH—, $(CH_3)_3C$—, $CH_3CH_2CH$ $(CH_3)$—, $(CH_3)_2$ $CHCH_2$—; B is H—, $CH_3$—, or a low alkyl; Z is H, —COOH, —$CONHR^2$, —$COR^2$; where $R^2$=H, —$NH_2$, —$NHR^3$ in which $R^3$ is —$CH_3$, low alkyl preferably —$CH_2CH(CH_3)_2$, or an amino acid or dipeptide in the carboxylic or amidated form preferably —Val—$NH_2$, —Val—OH, —Val—Lys—$NH_2$, —Val—Lys—OH, —Val—Lys(eN—Ac)—$NH_2$, —Val—Lys(eN—Ac)—OH, —Val—Ser—$NH_2$, —Val—Ser—OH, —Val—Gln—OH, —Val—Gln—$NH_2$. Lower alkyl typically means $C_1$–$C_6$ alkyl, for instance $C_1$–$C_4$ alkyl, such as methyl, ethyl, i-propyl, n-propyl, n-butyl, s-butyl, pentyl or hexyl. Long chain alkyl may be, for instance, $C_7$–$C_{30}$ alkyl, such as $C_{10}$–$C_{30}$ alkyl, $C_{12}$–$C_{30}$ alkyl, $C_{18}$–$C_{30}$ alkyl or $C_{20}$–$C_{30}$ alkyl; or $C_7$–$C_{25}$ alkyl, $C_{10}$–$C_{25}$ alkyl, $C_{10}$–$C_{20}$ alkyl, $C_{10}$–$C_{18}$ alkyl or $C_{12}$–$C_{25}$ alkyl. The alkyl groups in either case may be linear, branched or cyclic.

A functional derivative of the group —$OPO_3H_2$ is a structural analogue of the group which, when incorporated as group X in formula (I), functions in the same way as, or in a similar way to, —$OPO_3H_2$ itself.

In the context of the present invention the said "functional derivative" is a phosphoryl derivative which mimics the action of the group —$OPO_3H_2$ when incorporated as group X into general formula (I). The N-substituted amino acidic or peptidic residue in the definition of Y is suitably a residue of formula R—C(=O)—Z— wherein Z is a single amino acid residue or a chain of two or more amino acid residues, for instance a dipeptide or tripeptide, or an oligopeptide.

Examples of Z include —Gly—, —Thr— and —Ala—Thr—. In the definition of Y a polypeptide residue which includes an N-substituted amino acid or peptide moiety is a longer-chain peptide residue which includes an N-substituted moiety in its chain, for instance a moiety of formula R—C(=O)—Z— as defined above. Also longer peptides containing the above mentioned motifs are included.

According to the present invention the typical amino acid side chains have to be in the L configuration, having ascertained that the D analogues at every position are much less active. Indeed the unphosphorylated tyrosine containing forms. of the mentioned phosphopeptides or their mimics are also included in this patent, they being precursors of the actually active forms because they can be phosphorylated in vivo.

Representative compounds which are within the scope of the present invention and are specifically claimed, are the following (Ac means acetyl):

FCE 28405 Ac—Tyr($PO_3H_2$)—Val—Asn—Val—Lys—$NH_2$—Ex. 4 (SEQ ID No. 1)
FCE 28782 Ac—Tyr ($PO_3H_2$)—Val—Asn—Val—Lys (Ac)—$NH_2$—Ex. 5 (SEQ ID No. 2)
FCE 28539 Ac—Tyr($PO_3H_2$)—Val—Asn—Val—OH—Ex. 6 (SEQ ID No. 3)
FCE 28540 Ac—Tyr($PO_3H_2$)—Val—Asn—Val—$NH_2$—Ex. 1 (SEQ ID No. 4)
FCE 28404 $H_2O_3$PO—Ph—$CH_2$—$CH_2$—CO—Val—Asn—Val—OH—Ex. 7
FCE 29021 Ac—Tyr ($PO_3H_2$)—Val—Asn—$NHCH_2CH(CH_3)_2$—Ex. 3
FCE 29022 Ac—Tyr($PO_3H_2$)—Val—Asn—$NH_2$—Ex. 8
FCE 29018 Ac—Tyr($PO_3H_2$)—Val—$NHCH_2CH_2CONH_2$—Ex. 9
FCE 28615 Ac—Phe($CH_2PO_3H_2$)—Val—Asn—Val—Lys—$NH_2$—Ex. 10 (SEQ ID No. 5)
FCE 28995 Ac—Phe($CH_2SO_3H$)—Val—Asn—Val—$NH_2$—Ex. 12 (SEQ ID No. 6)
FCE 29406 Ac—Phe(p—$CH_2PO_3H_2$)—Val—Asn—$NH_2$—Ex. 11
FCE 29408 Ac—Phe(p—$CH_2PO_3H_2$)—Val—Asn—Val—$NH_2$—Ex. 2 (SEQ ID No. 7)
FCE 28785 Ac—Tyr($PO_3H_2$)—Val—Asn—Val—Ser—$NH_2$—Ex. 13 (SEQ ID No. 8)
FCE 28883 Ac—Tyr($PO_3H_2$)—Val—Asn—Val—Gln—$NH_2$—Ex. 14 (SEQ ID No. 9)
FCE 29128 6-biotinamido-hexanoyl-Tyr ($PO_3H_2$)—Val—Asn—Val—$NH_2$—Ex. 20 (SEQ ID No. 10)
FCE 29091 Ac—Tyr($PO_3Me_2$)—Val—Asn—Val—$NH_2$—Ex. 18 (SEQ ID No. 11)
FCE 29116 Ac—Tyr($PO_3HMe$)—Val—Asn—Val—$NH_2$—Ex. 18 (SEQ ID No. 12)
FCE 29145 Ac—Tyr($PO_3Et_2$)—Val—Asn—Val—$NH_2$—Ex. 19 (SEQ ID No. 13)
FCE 28702 Ac—Tyr($PO_3H_2$)—Ile—Asn—Gln—Ser—$NH_2$ (EGFR/Y1068)—Ex. 15 (SEQ ID No. 14)
FCE 28703 Ac—Tyr($PO_3H_2$)—Val—Asn—Ile—Glu—$NH_2$ (IRS1/Y895)—Ex. 16 (SEQ ID No. 15)
FCE 28737 Ac—Tyr($PO_3H_2$)—Ile—Asn—Ile—Lys—$NH_2$—Ex. 17 (SEQ ID No. 16)
FCE 29267 Ac—Tyr($PO_3H_2$)—Gly—Asn—$NH_2$—Ex. 21
FCE 29268 Ac—Phe(p—$CH_2PO_3H_2$)—Gly—Asn—$NH_2$—Ex. 22
FCE 29409 Ac—Tyr($PO_3H_2$)—Val—Gln—$NH_2$—Ex. 23
FCE 29410 Ac—Tyr($PO_3H_2$)—Val—D—Asn—$NH_2$—Ex. 24
FCE 29411 Ac—Tyr($PO_3H_2$)—Val—Hse—$NH_2$—Ex. 25
FCE 29413 Ac—Tyr($PO_3H_2$)—D—Val—Asn—$NH_2$—Ex. 26
FCE 29414 Ac—Tyr($PO_3H_2$)—Abu—Asn—$NH_2$—Ex. 27
FCE 29415 Ac—Tyr($PO_3H_2$)-terLeu—Asn—$NH_2$—Ex. 28
FCE 29421 Ac—Tyr($PO_3H_2$)—Ala—Asn—$NH_2$—Ex. 29
FCE 29475 Ac—Tyr($PO_3H_2$)—Aib—Asn—$NH_2$—Ex. 30
FCE 29402 $CH_3$—$(CH_2)_{12}$—CO—Gly—Gly—Tyr ($PO_3H_2$)—Val—Asn—Val—$NH_2$—Ex. 31 (SEQ ID No. 17)
FCE 29403 $CH_3$—$(CH_2)_{12}$—CO—Tyr ($PO_3H_2$)—Val—Asn—Val—$NH_2$—Ex. 32 (SEQ ID No. 18)
FCE 29404 $CH_3$—$(CH_2)_6$—CO—Tyr ($PO_3H_2$)—Val—Asn—Val—$NH_2$—Ex. 33 (SEQ ID No. 19)
FCE 29405 $C_6H_{11}$—$CH_2$—CO—Tyr ($PO_3H_2$)—Val—Asn—Val—$NH_2$—Ex. 34 (SEQ ID No. 20)
FCE 29407 $CH_3$—CO—$CH_2$—$CH_2$—CO—Phe (p—$CH_2PO_3H_2$)—Val—Asn—$NH_2$—Ex. 35

The compounds of the invention are chemically stable in solution at neutral pH, and can form pharmaceutically acceptable salts by acid or base addition depending on the nature of the peptide. All these forms are intended to be enclosed in the present invention. Suitable salts include base salts such as alkali metal salts (e.g. sodium or potassium salts) and ammonium salts; and acid addition salts such as hydrochloride, acetate and trifluoroacetate salts.

The peptides of the invention can be synthesized according to standard method such as those described in Escobedo, J. A., et al., Mol. Cell. Biol. 11: 1125–1132 (1991) or Turck, C. W. Peptide Res. 5: 156–160 (1992), for example using a protected prephosphorylated tyrosine residue. Alternatively the phosphopeptides can be prepared by introducing unprotected tyrosine and phosphorylating it after the peptide elongation either on solid or liquid phase.

In particular the peptides can be prepared by liquid or solid-phase methodologies known to those skilled in the art. (Schroeder et al., "The Peptides", Vol. I, Academic Press 1965, or Bodanszky et al., "Peptide Synthesis", Interscience Publishers, 1966, or McOmie (ed.) "Protective Group in Organic Chemistry", Plenum Press, 1973, or Barany et al., "The Peptides: Analysis, Synthesis, Biology" 2, Chapter 1, Academic Press, 1980). Thus, the invention includes a process for preparing a peptide of the invention, which process comprises chemically synthesizing the peptide from single amino acids and/or preformed peptides of two or more amino acid residues.

When it is wished to prepare a peptide in which a tyrosine residue is phosphorylated, a prephosphorylated protected tyrosine residue may be introduced during a solid phase synthesis, or a tyrosine residue of a protected preformed peptide may be phosphorylated while the peptide is attached to a solid support.

In the case of solid-phase synthesis any manual or automatic peptide synthesizer can be used and the peptides can be assembled in a stepwise manner on a resin support using either Boc or Fmoc strategies. All the reagents used as starting materials are on the market or may be produced and purified in accordance with methods known in the art.

The deprotected peptides are purified by reverse phase high performance liquid chromatography on a C18-Vydac column (Hesperia Calif.) in 0.05% trifluoroacetic acid by using a linear gradient of acetonitrile, and are isolated by lyophilization. All phosphopeptides are obtained as polyhydrated polytrifluoroacetates. The peptide content of all products is 65 to 90% and the chromatographic purity is more than 95% by HPLC peak relative integration at l=215–220 nm.

Amino acid analysis were carried out on acid hydrolysates (110° C. for 22 h in 6 N HCl+0.1% phenol). Alternatively a peptide containing a non-phosphorylated tyrosine can be first synthesized and subsequently a phosphate group can be introduced on the tyrosine residue either enzymatically or by chemical methods (in such a case the other functions susceptible of reaction with the phosphorylating agent must be suitably protected).

In this specification, the abbreviations used for amino acids and protecting groups are based on recommendations of the IUPAC-IUB Commission on Biochemical Nomenclature (see Eur. J. Biochem., vol 138, 9–37, 1984). In particular, the following abbreviations were used throughout the text: Boc, t-butyloxycarbonyl; tBu, t-butyl; Bzl, benzyl; ClZ, 4-chloro benzyloxycarbonyl; DIC, diisopropylcarbodiimide; DCM, dichloromethane; DIEA, diisopropylethylamine; DMF, dimethylformamide; DMS, dimethylsulfide; Dnp, dinitrophenyl; ECC, ethylchlorocarbonate; Fmoc, 9-fluorenylmethoxycarbonyl; NMM, N-methylmorpholine; NMP, N-methyl-2-pyrrolidone; RP-HPLC, reverse phase high performance liquid chromatography; TBTU, 2-(1H-benzotriazole-1-yl)-1,1,3,3-tetramethyluronium tetrafluoroborate; Trt, trityl.

The capacity of the peptides of the invention to inhibit the binding of cytosolic signal transducers to the tyrosine kinase receptors or to other tyrosine phosphorylated transducers can be assessed by binding inhibition experiments, such as the BIAcore analysis shown in the experimental section.

A further demonstration of the biological effects of the peptides of the invention is provided by their ability to interfere with the biological responses mediated by a receptor tyrosine kinase such as Hepatocyte Growth Factor Receptor (HGF-R) . As shown in the experimental section with a representative compound falling within the scope of the present invention, the peptides of the invention are able to interfere with the cell motility, cell proliferation, cell invasiveness and tubulogenesis mediated by HGF-R.

It is well known to the expert in the art that these biological responses are strictly associated to the occurrance of neoplastic diseases.The peptides of the invention can therefore be used in the treatment of the human or the animal body by therapy, for example in the treatment of a neoplastic disease.

The peptides of the invention are phosphorylated or unphosphorylated. The active form of the peptides is Igenerally phosphorylated, but it may be advantageous to administer a peptide in unphosphorylated form and allow the peptide to become phosphorylated inside the body of the patient. This is because the peptides may be more easily taken up into cells when unphosphorylated. The peptides of the invention may be administered to a patient by any convenient parenteral route as such or properly conjugated in order to increase enzymatic stability and cell permeability.

The choice of whether subcutaneous, intravenous or intramuscular administration is adopted; of the dose; of the frequency of administration depends upon a variety of factors. These factors include the purpose of the administration, the age and weight of the patient being treated and the condition of the patient. A therapeutically effective amount is given. Typically, however, the peptide is administered in an amount of from 10 to 1000 mg per dose, more preferably from 50 to 500 mg per dose, for each route of administration.The peptide may be formulated in a pharmaceutical composition. The pharmaceutical composition also comprises a pharmaceutically acceptable carrier or diluent. Any appropriate carrier or diluent may be employed, depending upon the route of administration.

Biological testing of the compounds.

The new compounds of the invention have been shown to inhibit particularly the binding of Grb2 trasducer to the phosphotyrosine docking site of HGF receptor; said compounds also inhibit the association of the the phosphotyrosine docking site containing proteins with other SH2 containing transducers (like p85-PI3K, PLCg, Src). Examples of this inhibitory activity are shown in table 1 and table 2.

BIAcore analysis.

Affinities were determined by biospecific interaction analysis with the BIAcore instrument (Jonsson, U. et al., *Biotechniques*, 1991, 11, 520–527; Jonsson, U. et al., In F. Turner (ed), Advances in Biosensors, vol. 2 JAI Press, London,1992, p. 291–336 ; Karlsson, R., et al., *J. Immunol. Meth.*, 1991, 145, 229–246). Relative affinities were determined by measuring the ability of the phosphopeptides to inhibit the interaction of the SH2 domains with an immobilized phosphopeptide (FCE 28942 6-biotinamido-hexanoyl—Gly—Gly—Gly—Gly—Gly—Ile—Gly—Glu—His—Tyr (PO$_3$H)—Val—His—Val—Asn—Ala—Thr—Tyr (PO$_3$H)—Val—Asn—Val—Lys—OH (SEQ ID No. 21) or FCE 28949 6-biotinamido-hexanoyl—Gly—Gly—Gly—Gly—Gly—Ile—Gly—Glu—His—Tyr—Val—His—Val—Asn—Ala—Thr—Tyr (PO$_3$H)—Val—Asn—Val–Lys—OH) (SEQ ID No. 22) which includes $Y_{1349}$ and $Y_{1356}$ in the human hepatocyte growth factor receptor. Table 1 and table 2 show the results of these measurements, expressed as % inhibition of binding of the transducers to a long biotinylated phosphopeptide (fixed to an Avidin loaded chip) representing the HGF receptor binding site for the considered transducers. Table 1 reports the data related to the inhibition of Grb2-SH2 interactions, while table 2 reports the inhibition data related to other transducers (p85, PLCg, Src). The more active compounds have been tested also in another system with the BIAcore technique, namely for their ability to inhibit the association between the flowing Grb2-SH2 or p85-SH2 and the whole cytosolic part of the HGF receptor in the full active phosphorylated form and immobilized on the chip. This last more representative but more laborious method has been found perfectly equivalent to the previous one using the immobilized long phosphopeptides.

TABLE 1

Inhibitory potency of representative compounds towards association with Grb2-SH2 domain.

|  |  | % of inhibition of Grb2-SH2 recognition | |
|---|---|---|---|
|  |  | 20 mM | 1 mM |
| FCE 28407 | H-Tyr (PO$_3$H$_2$)-Val-Asn-Val-Lys-OH (reference ) (SEQ ID No. 23) | 65 | 19 |
| FCE 28405 | Ac-Tyr (PO$_3$H$_2$)-Val-Asn-Val-Lys-NH$_2$ (SEQ ID No. 1) | 87 | 77 |
| FCE 28539 | Ac-Tyr (PO$_3$H$_2$)-Val-Asn-Val-OH (SEQ ID No. 3) | 100 | 82 |
| FCE 28540 | Ac-Tyr (PO$_3$H$_2$)-Val-Asn-Val-NH$_2$ (SEQ ID No. 4) | 100 | 77 |

TABLE 1-continued

Inhibitory potency of representative
compounds towards association with Grb2-SH2 domain.

| | | % of inhibition of Grb2-SH2 recognition | |
|---|---|---|---|
| | | 20 mM | 1 mM |
| FCE 29021 | Ac-Tyr(PO$_3$H$_2$)-Val-Asn-NHCH$_2$CH (CH$_3$)$_2$ | 93 | 56 |
| FCE 29022 | Ac-Tyr(PO$_3$H$_2$)-Val-Asn-NH$_2$ | 80 | 45 |
| FCE 29408 | Ac-Phe(p-CH$_2$PO$_3$H$_2$)-Val-Asn-Val-NH$_2$ (SEQ ID No. 7) | 90 | 50 |

TABLE 2

Inhibitory potency of representative compounds
towards association with other transducer-SH2 domains.

| | | % of inhibition of other SH2 recognitions | | | | | |
|---|---|---|---|---|---|---|---|
| | | PLCγ (C + N)SH2 | | p85 N-SH2 | | src SH2 | |
| | compound concentration: | 40 mM | 20 mM | 40 mM | 20 mM | 40 mM | 20 mM |
| FCE 28540 | Ac-Tyr(PO$_3$H$_2$)-Val-Asn-Val-NH$_2$ (SEQ ID No. 4) | 81 | 77 | 93 | 75 | 69 | 49 |
| FCE 29022 | Ac-Tyr(PO$_3$H$_2$)-Val-Asn-NH$_2$ | 60 | 60 | 63 | 50 | 35 | 14 |

Evaluation of the binding inhibition:

A) BIAcore analysis with immobilized biotinylated phosphopeptides.

The Biacore system provides a reliable and reproducible method to study the interaction between macromolecules. Binding is measured in real time under accurately controlled conditions, such as temperature and flow rate. Details of the construction and principle of operation of the BIAcore biosensor have been previously described (Panayotou et al., 1993). Protocols used were as follow: the SH2 domains used in these experiments were desalted through a Pharmacia column (Sephadex G-50 prepacked system) in order to achieve buffer exchange to the BIAcore running buffer, consisting of 20 mM Hepes, pH 7.4, 150 mM NaCl, 3.4 mM EDTA, 0.005% Tween 20 and 4 mM DTT. Experiments were performed using Sensor Chips (SA5, Pharmacia) on which streptavidin was preimmobilized on carboxymethylated dextran layer. Biotinylated phosphopeptides FCE 28949 (SEQ ID No. 22) and 28942 (SEQ ID No. 21), containig either the HGF receptor phosphotyrosine 1356 alone or the HGF receptor phosphotyrosines 1349 and 1356, were immobilized over the Streptavidinated Chip at a flow rate of 5 mL/sec for 50 sec. Non-specifically bound phosphopeptides were removed with a short pulse (4 sec) of 0.1% SDS. GST—SH2 domain fusion proteins were mixed with a range of concentrations (20 mM and 1 mM in most of the runs) of the examined competing phosphopeptides and injected over the surface at 5 mL/min for 120 sec at a constant temperature of 25° C. The material bound to the surface was removed with a 4 sec pulse of 0.1% SDS, which brought the signal to background level.

B) BIAcore analysis with immobilized GST/HGF-R fusion protein

The analysis was performed as described for the biotinylated phosphopeptides above. In these experiments, however, the purified GST/HGF-R was directly immobilized on the BIAcore chip. The GST/HGF-R (0.5 mg/mL) was immobilized on the sensor chip surface after activation with a 1:1 mixture of N-hydroxysuccinimide (NHS) and N-ethyl-N'-(3-dimethylaminopropyl)-carbodiimide hydrochloride (EDC) (Pharmacia). Excess reactive groups were blocked with ethanolamine (1.0 M).

The biological effects of the compounds were evalauted based on their ability to interefere with the biological responses mediated by the HGF-R including: (a) cell motility (b) cell proliferation (c) cell invasiveness (d) tubulogenesis.

Effects of the compounds on cell motility.

Upon HGF stimulation MDCK cells migrates (Stoker, M., E. Gherardi, M. Perryman, and J. Gray. Nature, 1987 327:239–242). This effect is mediated by the HGF-R which transduces motility signal. The ability of the compounds to inhibit HGF mediated cell motility was tested introducing the peptides in MDCK cells using a novel in situ electroporation technique called Cell Zapping (see the Experimental Procudure section below). The efficient delivery of the peptide to the cells was initially monitored using biotinylated peptides. After intracellular delivery biotinylated peptides were traced using fuoresceinated avidin. This approach showed that peptides were non toxic to the cells and stable for at least 24 hours. To evaluate the effect of the compounds on HGF-R mediated cell motility a scatter assay was performed using MDCK cells containing the electroporated compounds. Alternatively, these cells were seeded in a Transwell device (Costar), and stimulated to migrate across a porous membrane by HGF (see the Experimental Procudure section below). The effect of a representative compound on cell motility is shown in FIG. 1 A and FIG. 2. These experiments show that the compounds, for example FCE 29408 (SEQ ID No. 7), efficiently block cell motility, while a related peptide with phenylalanine at the place of the phosphotyrosine mimetic (FCE 29606 : Ac—Phe—Val—Asn—Val—OH) (SEQ ID No. 24) doesn't (negative control).

Effects of the compounds on cell proliferation

Upon HGF stimulation epithelial cells proliferate and this effect is mediated by the HGF-R (Medico, E., Mongiovi, A., Huff, J., Jelinek, M., Follenzi A., Gaudino, G., Parsons J. T. and Comoglio P. M., Mol. Biol. of the Cell, 1996, in press). The effects of the compounds on HGF-R mediated cell proliferation was monitored using the Cell Proliferation Assay (Amersham) (see the Experimental Procudure section below). Peptides were delivered to MDCK cells by cell zapping. The ability of the cells containing the compounds to incorporate the thymidine analogue 5-bromo-2'-deoxyuridine (BrdU) was then measured. The effect of representative compounds on cell proliferation is shown in FIG. 1 C. These experiments show that the compounds efficiently block cell proliferation, as shown for FCE 29408 (SEQ ID No. 7), in comparison with the negative reference FCE 29606 (SEQ ID No. 24).

Effects of the compounds on cell invasiveness

The HGF/SF receptor has a transforming counterpart in the constitutively active Tpr-Met protein (Ponzetto, C., Bardelli, A., Zhen, Z., Maina, F., Dalla Zonca, P., Giordano, S., Graziani, a., Panayotou, G. & Comoglio P. M. (1994) Cell 77, 1–20.) Tpr-Met transformed cells are higly tumorigenic in vivo and invade the extracellular matrix in vitro.

The effects of the compound on Tpr-Met mediated cell invasiveness was evaluated using a chemoinvasion assay (see the Experimental Procudure section below). Peptides were delivered to Tpr-Met transformed cells by cell zapping and the ability of the cells containing the compounds to invade a reconstituted basal membrane (Matrigel) was monitored. The effect of a representative compound on cell invasiveness is shown in FIG. 1 B. These experiments show that the compounds efficiently block cell invasiveness, as reported for FCE 29408 (SEQ ID No. 7), in comparison with the negative reference FCE 29606 (SEQ ID No. 24).

Effects of the compounds on tubulogenesis

Tubulogenesis is a complex morphological process in which epithelial cells organize themselves in tridimensional structures. When cultured in an environment mimicking the extracellular matrix, MDCK cells form tubules upon stimulation with HGF (Medico , E., Mongiovi, A., Huff, J., Jelinek, M., Follenzi A., Gaudino, G., Parsons J. T. and Comoglio P. M., Mol. Biol. of the Cell, 1996, in press) To test the effects of the compounds on this phenomenon, MDCK were supplied with the compounds to be evaluated, by cell zapping (see the Experimental Procudure section below). The monolayers, coated with a collagen matrix and grown in the presence of HGF, were monitored daily to observe tubules sprouting. FIG. 3 is a microphotograph showing the appearance of a two-days culture of electroporated MDCK. While the control peptide (negative reference FCE 29606: Ac—Phe—Val—Asn—Val—OH) (SEQ ID No. 24) allows cells to organize in normal tubular structures, FCE 29408 (SEQ ID No. 7) totally inhibits the tubulogenesis induced by HGF.

Examples illustrating the present invention are reported below without to be intended as a limitation to it.

BRIEF DESCRIPTION OF THE DRAWINGS

FIG. 2 is a microphotograph illustrating the biological effect of FCE 29408 (SEQ ID No. 7) on cell motility as discussed in the experimental section.

EXAMPLE 1

Figure 1A:
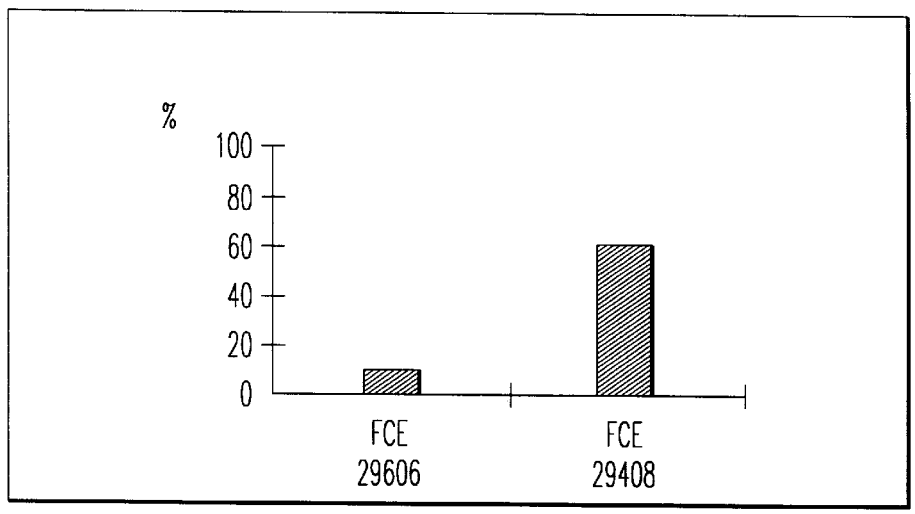
FIGS. 1(A–C) shows the effect of a representative compound of the invention (FCE 29408) (SEQ ID No. 7) on cell motility (FIG. 1A), cell invasion (FIG. 1B) and cell proliferation (FIG. 1C).In the ordinates of each graph it is shown the percentage of inhibition of motility (1A), invasion (1B) and proliferation (1C). FCE 29606 (SEQ ID No. 24) is used as negative control as explained in the experimental section.
Figure 1B:
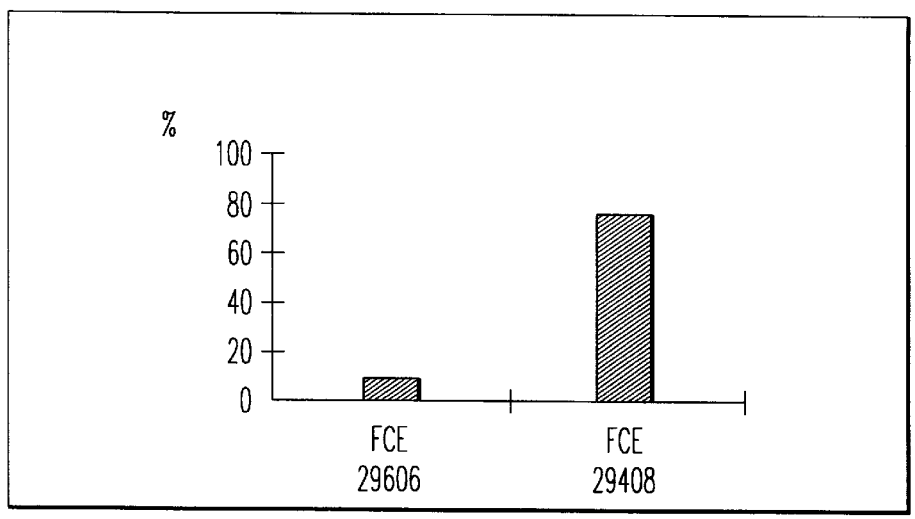
Figure 1C:
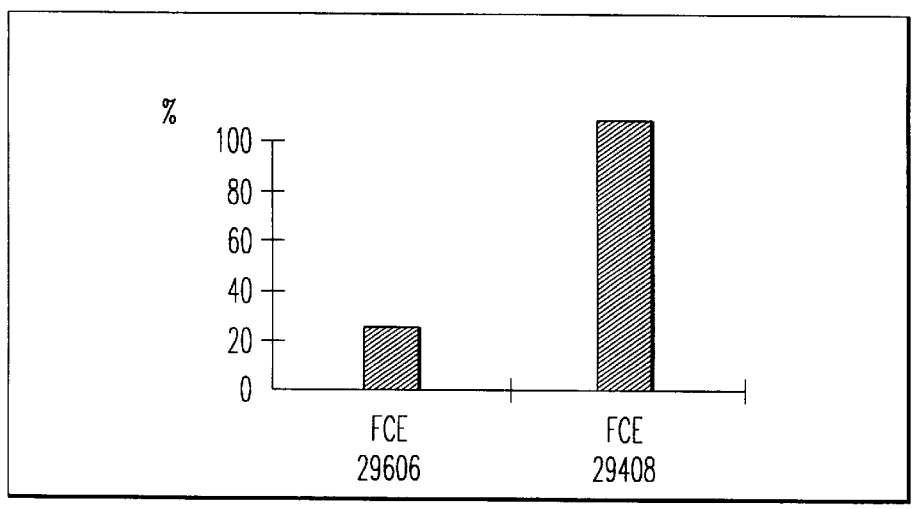
Figure 3A:
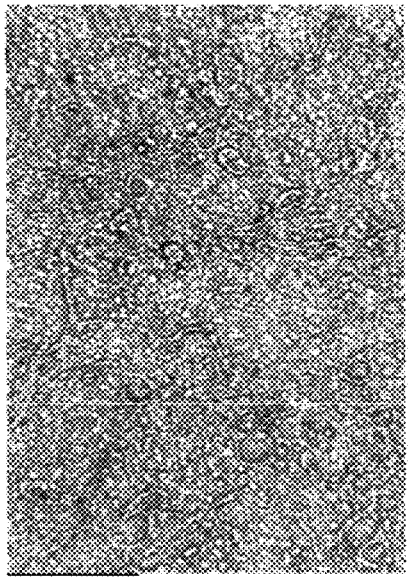
FIG. 3 is a microphotograph illustrating the inhibition of the tubulogenesis induced by HGF as explained in the experimental section and it shows the appearance of a two-days culture of electroporated MDCK.
Figure 3B:
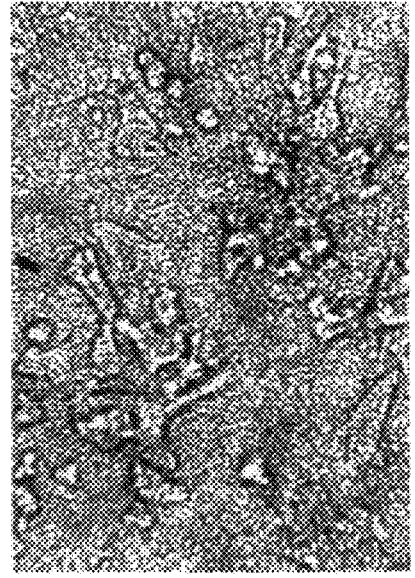

Preparation of Ac—Tyr (PO$_3$H$_2$)—Val—Asn—Val—NH$_2$ (FCE 28540)(SEQ ID No. 4)

The protected peptide on resin was synthesized by manual solid phase synthesis by sequential coupling of the following amino acids (in order of addition): Fmoc—Val—OH, Fmoc—Asn(Trt)—OH, Fmoc—Val—OH, Fmoc—Tyr—OH. After the last coupling the tyrosine residue was phosphorylated on solid phase (by using phosphoramidite chemistry and successive oxidation). The phosphorylation was followed by acidic treatment leading to side-chain deprotection and detachment from the resin. In detail 0.56g (0.25 mmol.) of Fmoc-2,4-dimethoxy-4'-(carboxymethyloxy) benzhydrylamine-aminomethyl-copoly(styrene-1% divinylbenzene) resin (Knorr) (0.45 mmol/g) were subjected to the following cycle comprising steps 1) to 5) of treatments:

1) NMP washing
2) piperidine (20%) in NMP
3) NMP, followed by DCM, followed by NMP
4) preformed 1-hydroxybenzotriazole ester (0.5 mmol) of Fmoc-amino acid in NMP
5) NMP, followed by DCM, followed by NMP Volumes of washes and reagents were 10 to 20 ml. Each step was repeated as many times as necessary for either complete reaction of the resin (steps 2,4) or complete displacement of the previous reagent from the resin (steps 1, 3, 5). Samples of resin were taken after each cycle washed by DCM and checked for completeness of reaction by a ninhydrin test.

1-hydroxybenzotriazole esters of Fmoc-amino acids were formed just prior to use by reacting Fmoc-amino acid (0.5 mmol.), 1-hydroxybenzotriazole (0.5 mmol.), DIEA (1 mmol) and TBTU (0.5 mmol.) in NMP.

The cycle of reactions, steps 1 to 5, was repeated for each amino acid residues such as to provide the sequence of the title compound. The following protected amino acids were added in the order: Fmoc—Val—OH, Fmoc—Asn(Trt)—OH, Fmoc—Val—OH, Fmoc—Tyr—OH. After the last cycle the peptidyl resin was washed several times with DCM and dried. A weight gain of 0.19 g was obtained with respect to the starting resin.

After the last cycle the phosphorylation of Tyr residue was obtained directly on the peptide still attached on the resin by treatment of the peptidyl resin with a solution of 30 eq. of 1H-tetrazole and 10 eq. of di-ter-butyl—N,N-diisopropylphosphoramidite in distilled THF for 1.5 h at 25° C. and subsequently with 30 eq. of ter-butylhydroperoxide in toluene for 1.5 h at 25° C. The N-terminal acetylation was obtained, after removal of N-terminal Fmoc-protecting group with 20% piperidine-DMF, by treatment of the peptidyl resin with 5 eq of acetic anhydride and 5 eq of DIEA in NMP for 30 min at 25° C. 0.79 g of the peptidyl resin was stirred with 20 ml of a mixture of trifluoroacetic acid/water 95:5 for 1.5 h at room temperature. Deprotected peptide was precipitated with diethylether and collected by filtration.

The crude peptide was purified by RP—HPLC on a C18-Vydac (Hesperia, Calif.) column (2,2×25 cm) in 0.05% trifluoroacetic acid using a linear gradient of acetonitrile in water from 5 to 32.5 % over 45 min. Fractions containing the product in pure form were combined, the acetonitrile was evaporated in vacuo and the remaining solution was lyophilized. The title compound was obtained (64 mg) with chromatographic purity (HPLC) of 99.9%.

Amino acid ratios: Val 2 (2); Asx 1.2 (1); Tyr 0.9 (1). Peptide content: 88%. FAB mass spectroscopy; m/z 615 [MH]$^+$. (MW 614.6)

EXAMPLE 2

Preparation of Ac—Phe(p—CH$_2$PO$_3$H$_2$)—Val—Asn—Val—NH$_2$ (FCE 29408) (SEQ ID No. 7)

Starting from 0.5 mmol of 4-(2',4'-dimethoxyphenyl-Fmoc-aminomethyl)phenoxyacetamido-norleucyl-4-methylbenzhydrylamine-polystyrene resin (Rink MBHA) the phosphonomethylpeptide was assembled on the resin in analogous manner as described in the example 1, adding the protected amino acids in the following order: Fmoc—Val—OH, Fmoc—Asn(Trt)—OH, Fmoc—Val—OH, Fmoc—Phe (p—CH$_2$PO$_3$Et$_2$)—OH. The N-terminal acetylation was obtained by treatment of the peptidyl resin with 5 eq of acetic anhydride and 5 eq of DIEA in NMP for 30 min at 25° C. The cleavage from the resin and the removal of the protecting groups, except the phosphonate ethyl groups, were carried out as described in example 1. The 270 mg of crude peptide were suspended in refluxing DCM with 1 mL of trimethylbromosilane for 2 h. After evaporation of the solvent the completely deprotected peptide was purified by RP—HPLC as described in Example 1 (but with acetonitrile gradient 5–43.5 %) giving the title compound with chromatographic purity (HPLC) of 98.0%. Amino acid ratios: Val 2 (2); Asx 1.3 (1). Peptide content: 100%. FAB mass spectroscopy: m/z 613 [MH]$^+$. (MW 612.6).

EXAMPLE 3

Preparation of Ac—Tyr (PO$_3$H$_2$)—Val—Asn—NHCH$_2$CH (CH$_3$)$_2$ (FCE 29021)

A different synthetic strategy has been conceived for the preparation of the title compound. The asparagine N-alkylamide has been introduced starting from the corresponding aspartic acid derivative N-alkylamidated at the a-carboxy group by linking the side-chain carboxy group to the amide-generating resin in order to have the b-amide group after the cleavage.

The noncommercial amino acid Fmoc—Asp—NH—CH$_2$—CH(CH$_3$)$_2$ was obtained by reaction of Fmoc—Asp (t.Bu)—OH (10 mmol) and isobutylamine (11 mmol) via mixed anhydride method with 10 eq of NMM and 10 eq of ECC for 4 h, followed by deprotection of t.butyl with a solution of TFA/water 95:5.

Starting from 0.35 mmol of Fmoc-4-methoxy-4'-(g-carboxypropyloxy)-benzhydrylamine-alanylaminomethyl-polystyrene resin (DOD) the phosphopeptide was assembled on the resin phosphorylated and acetylated in analogous manner as described in the example 1, adding the following amino acids in the order: Fmoc—Asp—NH—CH$_2$—CH (CH$_3$)$_2$, Fmoc—Val—OH, Fmoc—Tyr—OH. Using this resin the cleavage was performed at 37° C. for 2 h with the mixture TFA/H$_2$O/DMS 95:5:5. After evaporation of the solvent the completely deprotected peptide was purified by RP-HPLC as described in Example 1 giving the title compound with chromatographic purity (HPLC) of 99.8%. Amino acid ratios: Asx 0.9 (1); Val 1 (1); Tyr 1.1 (1). Peptide content: 73%. FAB mass spectroscopy: m/z 572 [MH]$^+$. (MW 571.6).

EXAMPLE 4

Preparation of Ac—Tyr (PO$_3$H$_2$)—Val—Asn—Val—Lys—NH$_2$ (FCE 28405) (SEQ ID No. 1)

The title compound was obtained by analogous manner as described in Example 1, but using an automatic synthesizer Applied Biosystem Peptide Synthesizer 430A, with chromatographic purity (HPLC) of 96.4%. FAB mass spectroscopy; m/z 743 [MH]$^+$. (MW 742.8).

EXAMPLE 5

Preparation of Ac—Tyr (PO$_3$H$_2$)—Val—Asn—Val—Lys (Ac)—NH$_2$ (FCE 28782) (SEQ ID No. 2)

The title compound was obtained by analogous manner as described in Example 1, with chromatographic purity (HPLC) of 98.9%. Amino acid ratios: Lys 1 (1); Val 1.73 (2); Asx 1.27 (1); Tyr 0.87 (1). Peptide content: 83%. FyAB mass spectroscopy; m/z 785 [MH]$^+$. (MW 784,8)

EXAMPLE 6

Preparation of Ac—Tyr (PO$_3$H$_2$)—Val—Asn—Val—OH (FCE 28539) (SEQ ID No. 3)

The title compound was obtained by analogous manner as described in Example 1, but using 4-hydroxymethylbenzyloxymethyl-copoly(styrene-1% divinylbenzene) resin (Wang). The first aminoacid, in this case FmocVal(Boc)OH, is loaded on the resin through its symmetric anhydride (generated by treatment of 12 equiv. of amino acid derivative with 6 equiv. of DIC in DCM for 20 min, filtration and evaporation) that dissolved in DMF is made to react with the resin in the presence of a catalitic amount of DMAP for 2 h. This loading was determined spectrophotometrically. The preparation was continued analogously to what is described in Example 1. The compound was obtained with chromatographic purity (HPLC) of 99.3%. Amino acid ratios: Val 1.6 (2); Asx 1 (1); Tyr 0.7 (1). Peptide content: 83%. FAB mass spectroscopy; m/z 616 [MH]$^+$. (MW 615.6)

EXAMPLE 7

Preparation of H$_2$O$_3$PO—Ph—CH$_2$—CH$_2$—CO—Val—Asn—Val—OH (FCE 29404)

The title compound was obtained by analogous manner as described in Example 6 for the use of the resin and the introduction of the first amino acid and analogously to Example 1 for the rest of the synthesis, but using an automatic synthesizer Applied Biosystem Peptide Synthesizer 430A. The compound was obtained, with chromatographic purity (HPLC) of 99.0%. Amino acid ratios: Val 1.9 (2); Asx 1 (1). Peptide content: 41%. FAB mass spectroscopy; m/z 559 [MH]$^+$. (MW 558.5)

EXAMPLE 8

Preparation of Ac—Tyr(PO$_3$H$_2$)—Val—Asn—NH$_2$ (FCE 29022)

The title compound was obtained by analogous manner as described in Example 1, but using Fmoc-4-methoxy-4'-(g-carboxypropyloxy)-benzhydrylamine-alanylaminomethyl-polystyrene resin (DOD) Using this resin the cleavage is performed at 37° C. for 2 h with the mixture TFA/H$_2$O/DMS 95:5:5. After evaporation of the solvent the completely deprotected peptide was purified by RP—HPLC as described in Example 1 giving the title compound with chromatographic purity (HPLC) of 98.7%. Amino acid ratios: Val 1 (1); Asx 1.3 (1); Tyr 0.9 (1). Peptide content: 81%. FAB mass spectroscopy; m/z 516 [MH]$^+$. (MW 515.5)

EXAMPLE 9

Preparation of Ac—Tyr (PO$_3$H$_2$)—Val—NHCH$_2$CH$_2$CONH$_2$ (FCE 29018)

The title compound was obtained by analogous manner as described in Example 8, but using Fmoc-bAlaOH instead of the Asn derivative. The compound was obtained with chromatographic purity (HPLC) of 97.0%. Amino acid ratios: Val 1 (1); Tyr 1.3 (1). Peptide content: 56%. FAB mass spectroscopy; m/z 473 [MH]$^+$. (MW 472.4)

EXAMPLE 10

Preparation of Ac—Phe (CH$_2$PO$_3$H$_2$)—Val—Asn—Val—Lys—NH$_2$ (FCE 28615) (SEQ ID No. 5)

The title compound was obtained by analogous manner as described in Example 2, but using Fmoc-2,4-dimethoxy-4'-

(carboxymethyloxy)benzhydrylamine-aminomethyl-copoly (styrene-1% divinylbenzene) resin (Knorr). The compound was obtained with chromatographic purity (HPLC) of 99.1%. Amino acid ratios: Lys 1 (1); Val 1.7 (2); Asx 1.1 (1). Peptide content: 95%. FAB mass spectroscopy; m/z 741 [MH]$^+$. (MW 740.8)

EXAMPLE 11

Preparation of Ac—Phe(p—CH$_2$PO$_3$H$_2$)—Val—Asn—NH$_2$ (FCE 29406)

The title compound was obtained by analogous manner as escribed in Example 2, with chromatographic purity (HPLC) of 98.4%. Amino acid ratios: Asx 1 (1); Val 0.8 (1). Peptide content: 100%. FAB mass spectroscopy; m/z 514 [MH]$^+$. (MW 513.5)

EXAMPLE 12

Preparation of Ac—Phe (CH$_2$SO$_3$H)—Val—Asn—Val—NH$_2$ (FCE 28995) (SEQ ID No. 6)

The title compound was obtained by analogous manner as described in Example 2, but using Fmoc-4-methoxy-4'-(g-carboxypropyloxy)-benzhydrylamine-alanylaminomethyl-polystyrene resin (DOD) and using FmocPhe(CH$_2$SO$_3$H)OH instead of the diethylphosphonylmethyl derivative. Using this resin the cleavage was performed at 37° C. for 2 h with the mixture TFA/H$_2$O/DMS 95:5:5. The compound was obtained with chromatographic purity (HPLC) of 97.0%. Amino acid ratios: Val 2 (2); Asx 1.1 (1). Peptide content: 69%. FAB mass spectroscopy; m/z 613 [MH]$^+$. (MW 612.7)

EXAMPLE 13

Preparation of Ac—Tyr (PO$_3$H$_2$)—Val—Asn—Val—Ser—NH2 (FCE 28785)(SEQ ID No. 8)

The title compound was obtained by analogous manner as described in Example 1, with chromatographic purity (HPLC) of 99.1%. Amino acid ratios: Ser 1 (1); Val 2.0 (2); Asx 1.2 (1); Tyr 0.9 (1). Peptide content: 97%. FAB mass spectroscopy; m/z 702 [MH]$^+$. (MW 701,7)

EXAMPLE 14

Preparation of Ac—Tyr(PO$_3$H$_2$)—Val—Asn—Val—Gln—NH$_2$ (FCE 29883) (SEQ ID No. 9)

The title compound was obtained by analogous manner as described in Example 1, with chromatographic purity (HPLC) of 96.5%. Amino acid ratios: Glx 1 (1); Val 1.7 (2); Asx 1.2 (1); Tyr 0.7 (1). Peptide content: 80%. FAB mass spectroscopy; m/z 743 [MH]$^+$. (MW 742,4)

EXAMPLE 15

Preparation of Ac—Tyr (PO$_3$H$_2$)—Ile—Asn—Gln—Ser—NH$_2$ (FCE 28702) (SEQ ID No. 14)

The title compound was obtained by analogous manner as described in Example 1, with chromatographic purity (HPLC) of 99.3%. Amino acid ratios: Ser 0.9 (1); Glx 1 (1); Asx 1.1 (1); Ile 0.8 (1); Tyr 0.7 (1). Peptide content: 92%. FAB mass spectroscopy; m/z 745 [MH]$^+$. (MW 744.7)

EXAMPLE 16

Preparation of Ac—Tyr (PO$_3$H$_2$)—Val—Asn—Ile—Glu—NH$_2$ (FCE 28703) (SEQ ID No. 15)

The title compound was obtained by analogous manner as described in Example 1, with chromatographic purity (HPLC) of 99.0%. Amino acid ratios: Asx 1 (1); Glx 0.9 (1); Ile 0.8 (1); Val 0.9 (1); Tyr 0.8 (1). Peptide content: 93%. FAB mass spectroscopy; m/z 796 [MNa]$^+$,758 [MH]$^+$, 515 [Ac—Tyr(PO$_3$H$_2$)—Val—Asn—NH$_2$]$^+$. (MW 756.7)

EXAMPLE 17

Preparation of Ac—Tyr (PO$_3$H$_2$) —Ile—Asn—Ile—Lys—NH$_2$ (FCE 28737) (SEQ ID No. 16)

The title compound was obtained by analogous manner as described in Example 1, with chromatographic purity (HPLC) of 93.0%. Amino acid ratios: Lys 1 (1); Ile 1.77 (2); Asx 1.17 (1); Tyr 0.8 (1). Peptide content: 78%. FAB mass spectroscopy; m/z 771 [MH]$^+$. (MW 770.8)

EXAMPLE 18

Preparation of Ac—Tyr(PO$_3$Me$_2$)—Val—Asn—Val—NH$_2$ (FCE 9091) (SEQ ID No. 11) and Preparation of Ac—Tyr(PO$_3$HMe)—Val—Asn—Val—NH$_2$ (FCE 29116) (SEQ ID No. 12)

The title compounds were obtained by analogous manner as described in Example 1, but using Fmoc-4-methoxy-4'-(g-carboxypropyloxy)-benzhydrylamine-alanylaminomethyl-polystyrene resin (DOD) and using FmocTyr(PO$_3$Me$_2$)OH instead of the tyrosine derivative hence skipping the phosphorylation step. Using this resin the cleavage was performed at 37° C. for 2 h with the mixture TFA/H$_2$O/DMS 95:5:5. The compounds were obtained as a mixture and separated by RP-HPLC.

Ac—Tyr (PO$_3$Me$_2$)—Val—Asn—Val—NH2 (FCE 29091) was obtained with chromatographic purity (HPLC) of 97.0%. Amino acid ratios: Val 2 (2); Asx 1.1(1); Tyr 0.9 (1). Peptide content: 83%. FAB mass spectroscopy: m/z 643 [MH]$^+$. (MW 642.63)

Ac—Tyr(PO$_3$HMe)—Val—Asn—Val—NH2 (FCE 29116) was obtained with chromatographic purity (HPLC) of 98.0%. Amino acid ratios: Val 2 (2); Asx 1.1 (1); Tyr 1.0 (1). Peptide content: 84%. FAB mass spectroscopy; m/z 651 [MNa]$^+$, 667 [MK]$^+$. (MW 628.6)

EXAMPLE 19

Preparation of BocTyrOBzl

The title compound was obtained by reaction of BocTyrOH (2 g, 7 mmol) and benzyl alcohol (0.873 ml, 8.4 mmol) with DCC (1.8 g, 8.75 mmol) and DMAP (85 mg, 0.7 mmol) for 1 h at 0 ° C. and 1 night at room temperature in THF. After the filtration of DCU, the solvent was concentrated in vacuo and the residue was dissolved in EtOAc and washed several times with a solution of NaHCO$_3$ 5% and of satured NaCl. The organic phase was dried (Na$_2$SO$_4$) and concentrated. The crude material was purified by silica gel chromatography. (Eluent:petroleum ether/ethyl acetate from 9/1 to 8/2 v/v) to give 1.5 g of the title compound (57% yield) H$^1$ NMR (200 MHz, CDCl$_3$) d (ppm)=7.4–6.65 (m, 9H, aromatics), 5.1 (d, 2H, COOCH$_2$F), 4.6 (m, 1H, N—CH—CO), 3.0 (d, 2H, CH—CH$_2$—F), 1.4 (s, 9H, tBu).

Preparation of BocTyr(PO$_3$Et$_2$)OBzl

The title compound was prepared by reaction of BocTyrOBzl (371 mg, 1 mmol) and diethylphosphorochloridate (258 mg, 1.5 mmol) with an excess of NaH (60% in mineral oil) in dry dioxane for 3.5 h at 50° C. under argon atmosphere The solvent was concentrated in vacuo and the residue was dissolved in EtOAc and washed several times with a 5% solution of NaHCO$_3$, a 10% solution of citric acid and a solution of satured NaCl. The organic phase was dried (Na$_2$SO$_4$) and concentrated, giving an oil 254 mg (50% yield), that was used without purification for the next step. FAB mass spectroscopy: m/z 508 [MH]$^+$, 530 [MNa]$^+$. H$^1$NMR (200 Mhz, CDCl$_3$) d (ppm)=7.4–6.85 (m, 9H, aromatics), 5.1 (d, 2H, COOCH$_2$—F), 4.6 (m, 1H, N—CH—CO), 4.3–4 (m, 4H, P—O—CH$_2$—CH$_3$), 3 (t, 2H, CH—CH$_2$—F), 1.4 (m, 15H, CH$_3$- CH$_{2+}$ tBu).

Preparation of BocTyr(PO$_3$Et$_2$)OH

The title compound was prepared by reaction of crude BocTyr(PO$_3$Et$_2$)OBzl (1 mmol) and ammonium formate (4 mmol) with 10% Pd on charcoal for 20 min. at 50° C. in methanol/acetic acid mixture. After the filtration of the catalyst the solvent was concentrated in vacuo and the residue was dissolved in EtOAc and washed several times with a solution of satured NaCl. The organic phase was dried (Na$_2$SO$_4$) and concentrated, giving an oil 270 mg (70% yield), that was used without purification for the next step. FAB mass spectroscopy: m/z 409 [MNa]$^+$. H$^1$NMR (200 mhz, DMSO-d$^6$) d (ppm)=7.3–7 (dd, 4H, aromatics), 4.1 (m, 4H, P—O—CH$_2$—CH$_3$), 3–2.7 (m, 2H, CH—CH$_2$—F), 1.4–1.2 (m, 15H, CH$_3$—CH$_2$+tBu).

Preparation of Ac—Tyr(PO$_3$Et$_2$)—Val—Asn—Val—NH$_2$ (FCE 29145) (SEQ ID No. 13)

The title compound was obtained by analogous manner as described in Example 18, but using BocTyr(PO$_3$Et$_2$)OH. The N-acetylation was performed by treatment of crude H—Tyr(PO$_3$Et$_2$)—Val—Asn—Val—NH$_2$ with 1.5 equiv. of DIEA and 5 equiv. of acetic anhydride in DMF for 2 h at 25° C. The final compound was obtained with chromatographic purity (HPLC) of 90.0%. Amino acid ratios: Val 2 (2); Asx 1.17 (1); Tyr 0.87 (1). Peptide content: 83%. FAB mass spectroscopy; m/z 671 [M—H]$^+$. (MW 670.1)

EXAMPLE 20

Preparation of 6-biotinamido-hexanoyl-Tyr (PO$_3$H$_2$)—Val—Asn—Val—NH$_2$ (FCE 29128) (SEQ ID No. 10)

The title compound was obtained by analogous manner as described in Example 8, but performing biotinylation instead of acetylation. The N-terminal biotinylation was obtained, after removal of N-terminal Fmoc-protecting group with 20% piperidine-DMF, by treatment of the peptidyl resin with 3.3 eq of sulfosuccinimidyl 6-(biotinamido) hexanoate and a few drops of N-methylmorpholine in DMF for 70 h at 25° C. ( till completeness of reaction checked by a ninhydrin test). The final compound was obtained with chromatographic purity (HPLC) of 98.8%. Amino acid ratios: Val 2 (2); Asx 1.2 (1); Tyr 1.0 (1). Peptide content: 97%. FAB mass spectroscopy; m/z 912 [M]. (MW 912.02)

EXAMPLE 21

Preparation of Ac—Tyr(PO$_3$H$_2$)—Gly—Asn—NE$_2$ (FCE 29267)

The title compound was obtained by analogous manner as described in Example 1, but using 4-(2',4'-dimethoxyphenyl-Fmoc-aminomethyl)phenoxyacetamido-norleucyl-4-methylbenzhydrylamine-polystyrene resin (Rink MBHA). The compound was obtained with chromatographic purity (HPLC) of 98.6%. Amino acid ratios: Asx 1 (1); Gly 0.9 (1); Tyr 0.8 (1). Peptide content: 77%. FAB mass spectroscopy; m/z 474 [MH]$^+$. (MW 473.4)

EXAMPLE 22

Preparation of Ac—Phe (p—CH$_2$PO$_3$H$_2$)—Gly—Asn—NH$_2$ (FCE 29268)

The title compound was obtained by analogous manner as described in Example 2, with chromatographic purity (HPLC) of 100%. Amino acid ratios: Asx 1 (1); Tyr 0.9 (1). Peptide content: 88%. FAB mass spectroscopy; m/z 472 [MH]$^+$. (MW 471.4)

EXAMPLE 23

Preparation of Ac—Tyr(PO$_3$H$_2$)—Val—Gln—NH$_2$ (FCE 29409)

The title compound was obtained by analogous manner as described in Example 1, but using 4-(2',4'-dimethoxyphenyl-Fmoc-aminomethyl)phenoxyacetamido-norleucyl-4-methylbenzhydrylamine-polystyrene resin (Rink MBHA). The compound was obtained with chromatographic purity (HPLC) of 99.3%. Amino acid ratios: Glx 1 (1); Val 0.8 (1); Tyr 0.8 (1). Peptide content: 81%. FAB mass. spectroscopy; m/z 530 [MH]$^+$. (MW 529.5)

EXAMPLE 24

Preparation of Ac—Tyr(PO$_3$H$_2$)—Val—D—Asn—NE$_2$ (FCE 29410)

The title compound was obtained by analogous manner as described in Example 23, with chromatographic purity (HPLC) of 99.0%. Amino acid ratios: Asx 1 (1); Val 0.8 (1); Tyr 0.9 (1). Peptide content: 87%. FAB mass spectroscopy; m/z 516 [MB]$^+$. (MW 515.5)

EXAMPLE 25

Preparation of Ac—Tyr(PO$_3$H$_2$)—Val—Hse—NH$_2$ (FCE 29411)

The title compound was obtained by analogous manner as described in Example 23, with chromatographic purity (HPLC) of 86.5%. Amino acid ratios: Val 0.8 (1); Tyr 1 (1). Peptide content: 88%. FAB mass spectroscopy; m/z 503 [MH]$^+$. (MW 502.5)

EXAMPLE 26

Preparation of Ac—Tyr (PO$_3$E$_2$)—D—Val—Asn—NH$_2$ (FCE 29413)

The title compound was obtained by analogous manner as described in Example 23, with chromatographic purity (HPLC) of 99.1%. Amino acid ratios: Asx 1 (1); Val 0.7 (1); Tyr 0.8 (1). Peptide content: 82%. FAB mass spectroscopy; m/z 516 [MH]$^+$. (MW 515.5)

EXAMPLE 27

Preparation of Ac—Tyr (PO$_3$H$_2$)—Abu—Asn—NH$_2$ (FCE 29414)

The title compound was obtained by analogous manner as described in Example 23, with chromatographic purity (HPLC) of 99.7%. Amino acid ratios: Asx 1 (1); Tyr 0.9 (1). Peptide content: 87%. FAB mass spectroscopy; m/z 502 [MH]$^+$. (MW 501.4)

EXAMPLE 28

Preparation of Ac—Tyr(PO$_3$H$_2$)-terLeu—Asn—NH$_2$ (FCE 29415)

The title compound was obtained by analogous manner as described in Example 23, with chromatographic purity (HPLC) of 98.7%. Amino acid ratios: Asx 1.2 (1); terLeu 1 (1); Tyr 1.0 (1). Peptide content: 77%. FAB mass spectroscopy; m/z 530 [MH]$^+$. (MW 529.5)

EXAMPLE 29

Preparation of Ac—Tyr(PO$_3$E$_2$)—Ala—Asn—NH$_2$ (FCE 29421)

The title compound was obtained by analogous manner as described in Example 23, with chromatographic purity (HPLC) of 98.9%. Amino acid ratios: Asx 1 (1); Ala 0.73 (1); Tyr 0.7 (1). Peptide content: 83%. FAB mass spectroscopy; m/z 488 [MH]$^+$. (MW 487)

EXAMPLE 30

Preparation of Ac—Tyr(PO$_3$H$_2$)—Aib—Asn—NH$_2$ (FCE 29475)

The title compound was obtained by analogous manner as described in Example 23, with chromatographic purity (HPLC) of 97.2%. Amino acid ratios: Asx 1 (1); Tyr 0.8 (1). Peptide content: 77%. FAB mass spectroscopy; m/z 502 [M-H]$^+$. (MW 501.44)

EXAMPLE 31

Preparation of CH$_3$—(CH$_2$)$_{12}$—CO—Gly—Gly—Tyr(PO$_3$H$_2$)—Val—Asn—Val—NH$_2$ (FCE 29402) (SEQ ID No. 17)

The title compound was obtained by analogous manner as described in Example 8, with capillar electrophoresis purity (EF) of 95%. Amino acid ratios: Val 2 (2); Asx 1.1 (1); Tyr 1.0 (1); Gly 1.9 (2). Peptide content: 94%. FAB mass spectroscopy; m/z 897 [M]. (MW 897.0)

EXAMPLE 32

Preparation of CH$_3$—(CH$_2$)$_{12}$—CO—Tyr(PO$_3$H$_2$)—Val—Asn—Val—NE$_2$ (FCE 29403) (SEQ ID No. 18)

The title compound was obtained by analogous manner as described in Example 8, with capillar electrophoresis purity (EF) of 95%. Amino acid ratios: Val 1.7 (2); Asx 1 (1); Tyr 0.8 (1). Peptide content: 87%. FAB mass spectroscopy; m/z 783 [MH]$^+$. (MW 782.9)

EXAMPLE 33

Preparation of CH$_3$—(CH$_2$)$_6$—CO—Tyr (PO$_3$H$_2$)—Val—Asn—Val—NH$_2$ (FCE 29404) (SEQ ID No. 19)

The title compound was obtained by analogous manner as described in Example 8, with capillar electrophoresis purity (EF) of 72%. Amino acid ratios: Val 1.8 (2); Asx 1 (1); Tyr 0.9 (1). Peptide content: 87%. FAB mass spectroscopy; m/z 699 [MH]$^+$. (MW 698.7)

EXAMPLE 34

Preparation of C$_6$H$_{11}$—CE$_2$—CO—Tyr(PO$_3$H$_2$)—Val—Asn—Val—NH$_2$ (FCE 29405) (SEQ ID No. 20)

The title compound was obtained by analogous manner as described in Example 8, with capillar electrophoresis purity (EF) of 75%. Amino acid ratios: Val 1.8 (2); Asx 1 (1); Tyr 1.0 (1). Peptide content: 96%. FAB mass spectroscopy; m/z 697 [MH]$^+$. (MW 696.7)

EXAMPLE 35

Preparation of CH$_3$—CO—CH$_2$—CH$_2$—CO—Phe (p—CH$_2$PO$_3$H$_2$)—Val—Asn—NH$_2$ (FCE 29407)

The title compound was obtained by analogous manner as described in Example 2, with chromatographic purity (HPLC) of 88.3%. Amino acid ratios: Asx 1 (1); Val 0.8 (1). Peptide content: 99%. FAB mass spectroscopy; m/z 570 [MH]$^+$. (MW 569.7)

EXAMPLE 36

Preparation of 6-biotinamido-hexanoyl—Gly—Gly—Gly—Gly—Gly—Ile—Gly—Glu—Bis—Tyr (PO$_3$B)—Val—His—Val—Asn—Ala—Thr—Tyr (PO$_3$H)—Val—Asn—Val—Lys—OH (FCE 28942) (SEQ ID No. 21)

Chain assembly was carried out on a MilliGen 9050 Peptide Synthesizer starting from a 4-hydroxymethylphenoxyacetamidomethyl-polyethylene glycol-polystyrene resin with the first amino acid, Fmoc—L—Lys(Boc)—OH already attached to the resin through an ester bound (1.1 g ; 0.18 mmol/g). The resin was subjected to the following cycle comprising a double coupling within the steps 1 to 6 of treatments:

1) removal of Fmoc-protecting group by using 20% piperidine—DMF, 7 minutes;

2) washes with DMF, 12 minutes;

3) first coupling with 4 equivalents of the Fmoc-amino acid derivative in DMF, 30 minutes;

4) washes with DMF, 8 minutes;

5) second coupling with 4 equivalents of the Fmoc-amino acid derivative in DMF, 30 minutes;

6) washes with DMF, 8 minutes;

The cycle of reactions, steps 1 to 6, was repeated for each amino acid residues such as to provide the sequence of the title compound, in the order from the carboxy-terminal to the amino-terminal, using the following side chain-protected amino acid derivatives: Fmoc—L—Asn(Trt)—OH, Fmoc—L—His(Boc)—OPfp, Fmoc—L—Glu(OtBu)—OPfp, Fmoc—L—Thr(tBu)—OR (where R is hydrogen or Pfp).

In each cycle the first coupling reaction (step 3) was carried out using Fmoc-amino acid pentafluorophenyl esters, with the exception of Fmoc—L—Asn(Trt)—OH, Fmoc—L—Tyr—OH, Fmoc—Gly—OH (in position 2 and 4 of peptide chain), which were coupled as 1-hydroxybenzotriazolyl esters, formed just prior to use by reacting Fmoc-amino acid, TBTU, 1-hydroxybenzotriazole (4 equivalents each) and N-methylmorpholine(8 equivalents). In each cycle the second coupling reaction (step 5) was carried out using Fmoc-amino acid 1-hydroxybenzotriazolyl esters formed just prior to use as described above, with the exception of Fmoc—L—Ala—OH, Fmoc—L—His(Boc)—OH, Fmoc—L—Glu(OtBu)—OH, which were coupled using their pentafluorophenyl esters.

After the last cycle the peptidyl resin was washed several times with DCM and dried. A weight gain of 1.2 g was obtained with respect to the starting resin. The phosphorylation of Tyr residue was obtained directly on the peptide still attached on the resin by treatment of the peptidyl resin with a solution of 30 eq. of 1H-tetrazole and 10 eq. of di-ter-butyl-N,N-diisopropyl-phosphoramidite in distilled THF for 1.5 h at 25° C. and subsequently with 30 eq. of ter-butylhydroperoxide in toluene for 1.5 h at 25° C. The N-terminal biotinylation was obtained, after removal of N-terminal Fmoc-protecting group with 20% piperidine-DMF, by treatment of the peptidyl resin with 3.3 eq of sulfosuccinimidyl 6-(biotinamido)hexanoate and a few drops of N-methylmorpholine in DMF for 70 h at 25° C. (till completeness of reaction checked by a ninhydrin test). The peptidyl resin was washed several times with DCM and dried. A weight gain of 1.5 g was obtained with respect to the starting resin. 0.70 g of the peptidyl resin were stirred with 8 ml of a mixture of trifluoroacetic acid/water/EMS 95:2.5:2.5 for 1.5 h at room temperature. Deprotected peptide was precipitated with diethylether and collected by filtration.

The crude peptide was purified by RP-HPLC on a C18-Vydac (Hesperia, Calif.) column (2,2×25 cm) with a flow rate of 18 ml/min by eluting with stepwise isocratic conditions successively at 13.25% for 25 min, 16% for 35 min, 18.75% for 30 min and 21.5% for 10 min of acetonitrile in 0.05 N AcONH4 aqueous solution, using an UV detector at 220 nm wavelenght. Fractions containing the product in pure form were combined, the acetonitrile was evaporated in vacuo and the remaining solution was lyophilized twice. The title compound was obtained (12 mg) with chromatographic purity (HPLC) of 91.5%. Amino acid ratios: Lys 1 (1); Asx 2.37 (2); Gly 6.00 (6); Ile 0.9 (1); Thr 1.00 (1); Ala 1.00 (1); His 1.73 (2); Glx 1.10 (1); Val 3.63 (4); Tyr 1.83 (2). Peptide content: 82%. FAB mass spectroscopy; m/z 2627.2 [M+H]$^+$; m/z 2625.5 [M−H]$^-$; (MW 2627.74)

EXAMPLE 37

Preparation of 6-biotinamido-hexanoyl—Gly—Gly—Gly—Gly—Gly—Ile—Gly—Glu—His—Tyr—Val—His—Val—Asn—Ala—Thr—Tyr (PO$_3$H)—Val—Asn—Val—Lys—OH (FCE 28949) (SEQ ID No. 22)

The title compound was obtained by analogous manner as described in Example 36, with chromatographic purity (HPLC) of 91.8%. Amino acid ratios: Lys 1 (1);. Val 3.67 (4); Asx 2.4 (2); Tyr 1.83 (2); Thr 1.0 (1); Ala 1.07 (1); His 1.6 (2); Glx 1.1 (1); Ile 0.93 (1); Gly 6.3 (6). Peptide content: 68%. FAB mass spectroscopy; m/z 2547.1 [M+H]$^+$;2545 [M−H]$^-$. (MW 2547.8)

EXAMPLE 38

Preparation of H—Tyr (PO$_3$H$_2$)—Val—Asn—Val—Lys—OH (FCE 28407) (as reference) (SEQ ID No.23)

The title compound was obtained by analogous manner as described in Example 6, but using an automatic synthesizer Applied Biosystem Peptide Synthesizer 430A, with the phosphorylation step as described in example 1. The compound was obtained with chromatographic purity (HPLC) of 99.0%. Amino acid ratios: Lys 0.8 (1); Val 1.6 (2); Asx 1 (1). Peptide content: 80%. FAB mass spectroscopy; m/z 702 [MH]$^+$. (MW 701.7)

EXAMPLE 39

Preparation of Ac—Phe—Val—Asn—Val—OH (FCE 29606) (as reference)(SEQ ID No. 24)

The title compound was obtained by analogous manner as described in Example 6 for the use of the resin and the introduction of the first amino acid and analogously to Example 1 for the rest of the synthesis. The compound was obtained with chromatographic purity (HPLC) of 97.6%. Amino acid ratios: Val 2 (2); Asx 1.4 (1); Phe 0.9 (1). Peptide content: 98%. FAB mass spectroscopy; m/z 520 [MH]$^+$. (MW 519.6)

EXAMPLE 40

Preparation of recombinant SE2 domains using bacterial expression systems

In order to rapidly produce large amounts of pure functional proteins, a procedure essentially as described by D. B. Smith and K. S. Johnson (Gene, 1988, 67, 31) was utilized. SH2 domains, as Glutathione-S-transferase (GST) fusion proteins, were obtained by polymerase chain reaction and cloned into the pGEX bacterial expression vector (Pharmacia). After bacterial expression the fusion proteins were readily purified using glutathione-agarose chromatography. Protocols used were as follow: *E-coli* cells (XL-1 Blue) transformed with the pGEX vector were grown overnight with shaking at 37° C. in 10 ml LB which were than was used to inoculate 1 L of LB media containing (100 g/ml) Ampicillin. This was grown for 3–4 hours with great aeration at 37° C. until OD$_{600}$=0.5—0.6. The expression of the recombinant protein was induced by the addition of IPTG to a final concentration of 0.2–0.4 mM and further growth for 4–8 h at 37° C. The bacterial cells were then pelleted by centrifugation for 15 min at 2000 g, washed in PBS twice and lysed on ice in 40 ml of EB buffer (100 mM Tris pH 7.4, 150 mM NaCl, 5 mM EDTA, 10% glycerol, 1% Triton X-100) containing protease inhibitors. The cells were subjected to mild sonication and then left on ice for a further 30 min. Cell debris was removed by centrifugation of the lysate at 14.000 rpm for 20 min at 4° C. The supernatant was incubated with 5 ml of glutathione agarose (Pharmacia) prewashed in EB buffer for 2 h with rotation at 4° C. to allow affinity binding of the recombinant protein. The beads were then washed 4×with EB, twice with 50 mM Tris-HCl [pH 8.0]. The protein was eluted off the beads by competition with 20 mM glutathione in 50 ml Tris-HCl [pH 8.0] and collected in 1 ml fractions which were assayed for protein content using BCA Protein Assay Reagent (Pierce). Purified GST-fusion proteins were then used for BIAcore and biochemical analyses.

EXAMPLE 41

Preparation of recombinant HGF-R using the Baculovirus expression system

The Intracellular domain of the human HGF-R cDNA as a GST fusion protein was inserted into the Baculovirus transfer vector PVL1393 (Invitrogen, San Diego, Calif.). The recombinant vector was cotransfected with the BsuI-digested BacPak6 viral DNA (Clontech Laboratories, Palo Alto, Calif.) into *Spodoptera frugiperda* insect cells (Sf9) by the Lipofectin procedure (Gibco-BRL, Gaithersburg, Md.). Positive clones were identified and purified by dot-blot hybridization and plaque assay. The recombinant virus was used to infect Sf9 cells with dilutions of $10^{31}$, $10^{-2}$, $10^{-3}$, $10^{-6}$. After one week, the infected cell extracts were blotted on a nylon filter and probed with radiolabelled full-length human HGF-R cDNA. The viruses containing the HGF-R cDNA gene were subsequently purified by plaque assay. Single viral clones were isolated and used for large scale infection of Sf9 cells. Expression of the viral clones was monitered by western blotting and high level expressing clones were subsequently used for large scale protein production. Purification of GST/HGF-R fusion protein was performed essentially as described for the SH2 domains.

EXAMPLE 42

Electroporation of adherent cells in situ: cell zapping

To efficiently introduce peptides into adherent cells a novel in situ electropermeation approach was used (L. Raptis and K. L. Firth, DNA and Cell Biology, 1990, 9, 615–621). This tecnique was preferred to conventional electroporation procedures since: (1) cell membranes are not modified by trypsin treatment (2) cells are not subjected to the added stress of detachment from substratum (3) cell viability is higher than in normal electroporation procedure (4) cell modification can be examined direclty by microscopic inspection after the electroporation. The electroporation device (Epizap EZ-11. Ask Science Inc., Kingston, Ontario, Calif.) consisted of a circuit for charging and discharging a capacitor and an assembly for delivering the pulse to the cells. The latter consisted of a glass slide coated with electrically conductive, optically transparent indiumtin oxide, an alluminium negative electrode and an alluminium positive electrode. The day before the experiment, the glass slide was placed inside a 10 cm petri dish and sterilized with ethanol. MDCK cells were plated on the conductive surface. Prior to pulse application, the growth medium (DMEM 10% FCS) was removed and the cells were washed twice with the electroporation buffer (10 mM sodium phosphate pH 7.0, 140 mM NaCl, 1 mM KCl). The same buffer supplemented with the compounds under examination to be introduced (as a 1 mM solution in electroporation buffer), was subsequently added to the cells. Electroporation was performed as a single pulse according to the following parameters: 50–100V and 1–20 mF. After the pulse cells were washed twice with growth medium and allowed to recover for 2 hours at 37° C. Cells viability was assessed by the addition of trypan blue 2 hours after electroporation. Electroporated cells were then detached from the glass slide and directly used in the migration and invasion assays.

EXAMPLE 43

Transwell migration and invasion assays

Stimulation of cell invasiveness was determined using a Costars culture chambers transwell (6.5 mm, Costar Corporation, Cambridge, Mass.). Polycarbonate membranes (8 mm pore size) on the bottoms of the upper compartment of the transwells were used. After electroporation with the compounds under evaluation as described in example 47, 105 cells in 200 ml of medium were placed on the polycarbonate membrane in the upper compartment. One ml of DMEM 5% FCS, alone or containing the stimulating factor (400 units of highly purified HGF), was added to the lower compartment. The plates were incubated at 37° C. in a 5% $CO_2$ atmosphere saturated with $H_2O$ for 24h. At the end of incubation, the cells at the upper side of the polycarbonate filter were mechanically removed. When testing cell invasiveness polycarbonate filters were coated with 1.2 mg/ml matrigel mimicking the epithelial basal membrane structure and containing: type IV collagen, laminin and other basal membrane components (Collaborative Research Incorporated, Waltham, Mass.). When evaluating cell invasion incubation was extended up to 48 hours. Cells that had migrated to the lower side of the filter were fixed with 11% glutheraldeyde for 15 min at room temperature, washed three times with distilled water and stained with 0.1% crystal violet-20% methanol for 20' at room temperature. After three washes with water and complete drying at room temperature, the crystal violet was solubilized by immersing the filters in 300 ml of 10% acetic acid (5' at room temperature). The concentration of the solubilized crystal violet was evaluated as absorbance at 590 nm.

EXAMPLE 44

Cell proliferation assay

Stimulation of cell proliferation was measured by incorporation of the thymidine analogue 5-bromo-2'-deoxyuridine (BrdU) using the Cell Proliferation Assay (Amersham). MDCK cells after electroporation with the compounds under evaluation as described in example 47, were plated in microtitre plate to reach subconfluence, starved in DMEM 0.2% FCS for 24–48h, then stimulated with purified recombinant HGF. After 6 h, BrdU was added and left to incorporate for a further 2 h. Incorporated BrdU was detected by a specific monoclonal antibody and a peroxidase-conjugated secondary antibody. Incubation with chromogen peroxidase substrate yields a soluble green dye, readable as absorbance at 410 nm.

EXAMPLE 45

Tubulogenesis assay

The traditional tubulogenesis assay (Medico et al., 1996) was modified to be performed in situ with electroporated cells. MDCK cells were grown to Iconfluence in DMEM 10% FCS on conductive slides. After zapping with the compounds under evaluation as described in example 47, MDCK were coated by an artificial extracellular matrix, containing a 2% mixture of purified collagens, mainly type I (Seromed). The coated monolayers were cultured in the presence of purified recombinant HGF for 4–5 days. Every second day the HGF supplemented medium was refreshed. Tubulogenesis was monitored by daily observation with an inverted optical microscope (Leica) at a 400×magnification. After two days of HGF stimulation tubular structure became evident.

What is claimed is:

1. A peptide represented by formula (I):

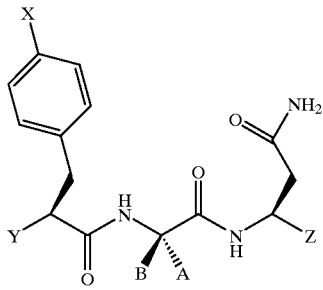

(I)

wherein

Y is hydrogen or R—C(=O)NH— wherein R is hydrogen, lower alkyl or long chain alkyl, the alkyl group in either case being linear, branched or cyclic;

X is —OPO$_3$H$_2$ or a finctional derivative thereof;

A is lower alkyl,

B is H— or lower alkyl;

Z is H, —COOH, —CONHR$^2$, —COR$^2$ wherein R$^2$=H, —NH$_2$, —NHR$^3$ in which R$^3$ is lower alkyl, or an amino acid or dipeptide in the carboxylic or amidated form;

or a pharmaceutically acceptable salt thereof, with the proviso that Ac—Y(X)—V—N—V—Q—NH$_2$, Ac—Y(X)—V—N—V—NH$_2$, and Ac—Y(X)—V—N—NH$_2$, wherein X is as defined above, are excluded.

2. The peptide of claim 1, wherein the finctional derivative of —OPO$_3$H$_2$ is selected from the group consisting of —CH$_2$PO$_3$H$_2$, —CF$_2$PO$_3$H$_2$, —CHFPO$_3$H$_2$, —CH$_2$SO$_3$H, —CF$_2$SO$_3$H, —CHFSO$_3$H, —SPO$_3$H$_2$, —OPSO$_2$H$_2$, —SPSO$_2$H$_2$, —OPS$_2$OH$_2$, —OP(CH$_3$)O$_2$H, —SP(CH$_3$)O$_2$H, —OP(CH$_3$)SOH, OP(CF$_3$)O$_2$H, —OP(CHF$_2$)O$_2$H, —SP(CF$_3$)O$_2$H, —SP(CHF$_2$)O$_2$H, and the lower alkyl esters thereof.

3. The peptide of claim 2, wherein X is —OPO$_3$H$_2$, —CH$_2$SO$_3$H, or a lower alkyl ester thereof.

4. The peptide of claim 1, wherein A is CH$_3$, CH$_3$CH$_2$—, (CH$_3$)$_2$CH—, (CH$_3$)$_3$C—, CH$_3$CH$_2$CH(CH$_3$)—, or (CH$_3$)$_2$CHCH$_2$—.

5. The peptide of claim 1, wherein R$^3$ is selected from the group consisting of —CH$_2$CH(CH$_3$)$_2$, —Val—NH$_2$, —Val—OH, —Val—Lys—NH$_2$, —Val—Lys—OH, —Val—Lys(eN—Ac)—NH$_2$, —Val—Lys(eN—Ac)—OH, —Val—Ser—NH$_2$, —Val—Ser—OH, —Val—Gln—OH and —Val—Gln—NH$_2$.

6. A process for preparing the peptide of claim 1, comprising chemically synthesizing the peptide represented by formula (I) from single amino acids and/or preformed peptides of two or more amino acid residues.

7. The process of claim 6, wherein a prephosphorylated protected tyrosine residue is introduced into the peptide during solid phase synthesis.

8. The process of claim 6, wherein a tyrosine residue of a protected preformed peptide is phosphorylated while the peptide is attached to a solid support.

9. The process of claim 6, which comprises converting the peptide into a pharmaceutically acceptable salt thereof.

10. A pharmaceutical composition, comprising a physiologically acceptable carrier or diluent, and the peptide of claim 1.

11. A method of treating a neoplastic disease, comprising administering an effective amount of the peptide of claim 1 to a patient in need thereof.

12. A peptide represented by formula (I):

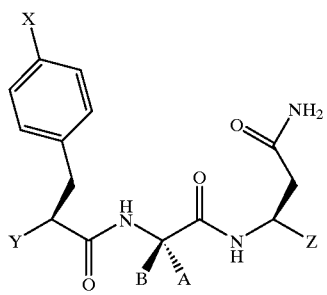

(I)

wherein

Y is R—C(=O)—Gly—, R—C(=O)—Thr— or R—C(=O)—Ala—Thr—, wherein R is hydrogen, lower alkyl or long chain alkyl, the alkyl group in either case being linear, branched or cyclic, an N-substituted amino acid or peptide residue or a polypeptide residue or a polypeptide residue which includes an N-substituted amino acid or peptide moiety;

X is —OPO$_3$H$_2$ or a fimctional derivative thereof;

A is lower alkyl,

B is H— or lower alkyl;

Z is H, —COOH, —CONHR², —COR² wherein R²=H, —NH₂, —NHRW in which R³ is lower alkyl, or an amino acid or dipeptide in the carboxylic or amidated form;

or a pharmaceutically acceptable salt thereof, with the proviso that Val—Asn—Ala—Thr—Tyr(X)—Val—Asn—Val—Lys, wherein X is as defined above, and Ile—Gly—Glu—His—Tyr—Val—His—Val—Asn—Ala—Thr—Tyr—Val—Asn—Val—Lys, wherein the Tyr at position 5 or 13 mau be substituted with X, wherein X is as defined above are excluded.

13. The peptide of claim 12, wherein the fuinctional derivative of —OPO₃H₂ is selected from the group consisting of —CH₂PO₃H₂, —CF₂PO₃H₂, —CHFPO₃H₂, —CH₂SO₃H, —CF₂SO₃H, —CHFSO₃H, —SPO₃H₂, —OPSO₂H₂, —SPSO₂H₂, —OPS₂OH₂, —OP(CH₃)O₂H, —SP(CH₃)O₂H, —OP(CH₃)SOH, OP(CF₃)O₂H, —OP(CHF₂)O₂H, —SP(CF₃)O₂, H, —SP(CHF₂)O₂, H and the lower alkyl esters thereof.

14. The peptide of claim 13, wherein X is —OPO₃H₂, —CH₂SO₃H, or a lower alkyl ester thereof.

15. The peptide of claim 12, wherein A is CH₃, CH₃CH₂—, (CH₃)₂CH—, (CH₃)₃C—, CH₃CH₂CH(CH₃)—, or (CH₃)₂CHCH₂—.

16. The peptide of claim 12, wherein R³ is selected from the group consisting of —CH₂CH(CH₃)₂, —Val—NH₂, —Val—OH, —Val—Lys—NH₂, —Val—Lys—OH, —Val—Lys(eN—Ac)—NH₂, —Val—Lys(eN—Ac)—OH, —Val—Ser—NH₂, —Val—Ser—OH, —Val—Gln—OH and —Val—Gln—NH₂.

17. A process for preparing the peptide of claim 12, comprising chemically synthesizing the peptide represented by formula (I) from single amino acids and/or preformed peptides of two or more amino acid residues.

18. The process of claim 17, wherein a prephosphorylated protected tyrosine residue is introduced into the peptide during solid phase synthesis.

19. The process of claim 17, wherein a tyrosine residue of a protected preformed peptide is phosphorylated while the peptide is attached to a solid support.

20. The process of claim 17, which comprises converting the peptide into a pharmaceutically acceptable salt thereof.

21. A pharmaceutical composition, comprising a physiologically acceptable carrier or diluent, and the peptide of claim 12.

22. A method of treating a neoplastic disease, comprising administering an effective amount of the peptide of claim 12 to a patient in need thereof.

23. A peptide selected from the group consisting of

Ac—Tyr(PO₃H₂)—Val—Asn—Val—Lys—NH₂,
Ac—Tyr(PO₃H₂)—Val—Asn—Val—Lys(Ac)—NH₂,
Ac—Tyr(PO₃H₂)—Val—Asn—Val—OH,
H₂O₃PO—Ph—CH₂—CH₂—CO—Val—Asn—Val—OH,
Ac—Tyr(PO₃H₂)—Val—Asn—NHCH₂CH(CH₃)₂,
Ac—Tyr(PO₃H₂)—Val—NHCH₂CH₂CONH₂,
Ac—Phe(CH₂PO₃H₂)—Val—Asn—Val—Lys—NH₂,
Ac—Phe(CH₂SO₃H)—Val—Asn—Val—NH₂,
Ac—Phe(p—CH₂PO₃H₂)—Val—Asn—NH₂,
Ac—Phe(p—CH₂PO₃H₂)—Val—Asn—Val—NH₂,
Ac—Tyr(PO₃H₂)—Val—Asn—Val—Ser—NH₂,
6-biotinamido-hexanoyl-Tyr(PO₃H₂)—Val—Asn—Val—NH₂,
Ac—Tyr(PO₃Me₂)—Val—Asn—Val—NH₂,
Ac—Tyr(PO₃HMe)—Val—Asn—Val—NH₂,
Ac—Tyr(PO₃Et₂)—Val—Asn—Val—NH₂,
Ac—Tyr(PO₃H₂)—Ile—Asn—Gln—Ser—NH₂,
Ac—Tyr(PO₃H₂)—Val—Asn—Ile—Glu—NH₂,
Ac—Tyr(PO₃H₂)—Ile—Asn—Ile—Lys—NH₂,
Ac—Tyr(PO₃H₂)—Gly—Asn—NH₂,
Ac—Phe(p—CH₂PO₃H₂)—Gly—Asn—NH₂,
Ac—Tyr(PO₃H₂)—Val—Gln—NH₂,
Ac—Tyr(PO₃H₂)—Val—D—Asn—NH₂,
Ac—Tyr(PO₃H₂)—Val—Hse—NH₂,
Ac—Tyr(PO₃H₂)—D—Val—Asn—NH₂,
Ac—Tyr(PO₃H₂)—Abu—Asn—NH₂,
Ac—Tyr(PO₃H₂)-terLeu—Asn—NH₂,
Ac—Tyr(PO₃H₂)—Ala—Asn—NH₂,
Ac—Tyr(Po₃H₂)—Aib—Asn—NH₂,
CH₃—(CH₂)₁₂—CO—Gly—Gly—Tyr(PO₃H₂)—Val—Asn—Val—NH₂,
CH₃—(CH₂)₁₂—CO—Tyr(PO₃H₂)—Val—Asn—Val—NH₂,
CH₃—(CH₂)₆—CO—Tyr(PO₃H₂)—Val—Asn—Val—NH₂,
C₆H₁₁—CH₂—CO—Tyr(PO₃H₂)—Val—Asn—Val—NH₂, and
CH₃—CO—CH₂—CH₂—CO—Phe(p—CH₂PO₃H₂)—Val—Asn—NH₂, or a pharmaceutically acceptable salt thereof.

24. A process for preparing the peptide of claim 23, comprising chemically synthesizing the peptide from single amino acids and/or preformed peptides of two or more amino acid residues.

25. The process of claim 24, wherein a prephosphorylated protected tyrosine residue is introduced into the peptide during solid phase synthesis.

26. The process of claim 24, wherein a tyrosine residue of a protected preformed peptide is phosphorylated while the peptide is attached to a solid support.

27. The process of claim 24, which comprises converting the peptide into a pharmaceutically acceptable salt thereof.

28. A pharmaceutical composition, comprising a physiologically acceptable carrier or diluent, and the peptide of claim 23.

29. A method of treating a neoplastic disease, comprising administering an effective amount of the peptide of claim 23 to a patient in need thereof.

30. The peptide of claim 23, which is selected from the group consisting of

Ac—Tyr(PO₃H₂)—Val—Asn—Val—Lys—NH₂,
Ac—Tyr(PO₃H₂)—Val—Asn—Val—Lys(Ac)—NH₂,
Ac—Tyr(PO₃H₂)—Val—Asn—Val—OH,
H₂O₃PO—Ph—CH₂—CH₂—CO—Val—Asn—Val—OH,
Ac—Tyr(PO₃H₂)—Val—Asn—NHCH₂CH(CH₃)₂,
Ac—Tyr(PO₃H₂)—Val—NHCH₂CH₂CONH₂, and
Ac—Phe(CH₂PO₃H₂)—Val—Asn—Val—Lys—NH₂, or a pharmaceutically acceptable salt thereof.

31. The peptide of claim 23, which is selected from the group consisting of

Ac—Phe(CH₂SO₃H)—Val—Asn—Val—NH₂,
Ac—Phe(p—CH₂PO₃H₂)—Val—Asn—NH₂,
Ac—Phe(p—CH₂PO₃H₂)—Val—Asn—Val—NH₂,

Ac—Tyr($PO_3H_2$)—Val—Asn—Val—Ser—$NH_2$,
6-biotinamido-hexanoyl-Tyr($PO_3H_2$)—Val—Asn—Val—$NH_2$,
Ac—Tyr($PO_3Me_2$)—Val—Asn—Val—$NH_2$,
Ac—Tyr($PO_3HMe$)—Val—Asn—Val—$NH_2$,
Ac—Tyr($PO_3Et_2$)—Val—Asn—Val—$NH_2$, and
Ac—Tyr($PO_3H_2$)—Ile—Asn—Gln—Ser—$NH_2$,
or a pharmaceutically acceptable salt thereof.

32. The peptide of claim 23, which is selected from the group consisting of
Ac—Tyr($PO_3H_2$)—Val—Asn—Ile—Glu—$NH_2$,
Ac—Tyr($PO_3H_2$)—Ile—Asn—Ile—Lys—$NH_2$,
Ac—Tyr($PO_3H_2$)—Gly—Asn—$NH_2$,
Ac—Phe(p—$CH_2PO_3H_2$)—Gly—Asn—$NE_2$,
Ac—Tyr($PO_3H_2$)—Val—Gln—$NH_2$,
Ac—Tyr($PO_3H_2$)—Val—D—Asn—$NH_2$,
Ac—Tyr($PO_3H_2$)—Val—Hse—$NH_2$, and
Ac—Tyr($PO_3H_2$)—D—Val—Asn—$NH_2$,
or a pharmaceutically acceptable salt thereof.

33. The peptide of claim 23, which is selected from the group consisting of
Ac—Tyr($PO_3H_2$)—Abu—Asn—$NH_2$,
Ac—Tyr($PO_3H_2$)-terLeu—Asn—$NH_2$,
Ac—Tyr($PO_3H_2$)—Ala—Asn—$NH_2$,
Ac—Tyr($PO_3H_2$)—Aib—Asn—$NH_2$,
$CH_3$—$(CH_2)_{12}$—CO—Gly—Gly—Tyr($PO_3H_2$)—Val—Asn—Val—$NH_2$,
$CH_3$—$(CH_2)_{12}$—CO—Tyr($PO_3H_2$)—Val—Asn—Val—$NH_2$,
$CH_3$—$(CH_2)_6$—CO—Tyr($PO_3H_2$)—Val—Asn—Val—$NH_2$,
$C_6H_{11}$—$CH_2$—CO—Tyr($PO_3H_2$)—Val—Asn—Val—$NH_2$, and
$CH_3$—CO—$CH_2$—$CH_2$—CO—Phe(p—$CH_2PO_3H_2$)—Val—Asn—$NH_2$,
or a pharmaceutically acceptable salt thereof.

* * * * *

SEQUENCE LISTING

<160> NUMBER OF SEQ ID NOS: 24

<210> SEQ ID NO 1
<211> LENGTH: 5
<212> TYPE: PRT

```
<213> ORGANISM: Artificial Sequence
<220> FEATURE:
<221> NAME/KEY: MOD_RES
<222> LOCATION: (1)
<223> OTHER INFORMATION: Xaa at position 1 is Ac-Tyr(PO3H2)
<221> NAME/KEY: MOD_RES
<222> LOCATION: (5)
<223> OTHER INFORMATION: Xaa at position 5 is Lys-NH2
<223> OTHER INFORMATION: Description of Artificial Sequence:modified
      peptide

<400> SEQUENCE: 1

Xaa Val Asn Val Xaa
  1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence:modified
      peptide
<221> NAME/KEY: MOD_RES
<222> LOCATION: (1)
<223> OTHER INFORMATION: Xaa at position 1 is Ac-Tyr(PO3H2)
<221> NAME/KEY: MOD_RES
<222> LOCATION: (5)
<223> OTHER INFORMATION: Xaa at position 5 is Lys(Ac)-NH2

<400> SEQUENCE: 2

Xaa Val Asn Val Xaa
  1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence:modified
      peptide
<221> NAME/KEY: MOD_RES
<222> LOCATION: (1)
<223> OTHER INFORMATION: Xaa at position 1 is Ac-Tyr(PO3H2)
<221> NAME/KEY: MOD_RES
<222> LOCATION: (4)
<223> OTHER INFORMATION: Xaa at position 4 is Val-OH

<400> SEQUENCE: 3

Xaa Val Asn Xaa
  1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence:modified
      peptide
<221> NAME/KEY: MOD_RES
<222> LOCATION: (1)
<223> OTHER INFORMATION: Xaa at position 1 is Ac-Tyr(PO3H2)
<221> NAME/KEY: MOD_RES
<222> LOCATION: (4)
<223> OTHER INFORMATION: Xaa at position 4 is Val-NH2

<400> SEQUENCE: 4

Xaa Val Asn Xaa
  1

<210> SEQ ID NO 5
<211> LENGTH: 5
```

```
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa at position 1 is Ac-Phe(CH2PO3H2)
<221> NAME/KEY: MOD_RES
<222> LOCATION: (5)
<223> OTHER INFORMATION: Xaa at position 5 is Lys-NH2
<223> OTHER INFORMATION: Description of Artificial Sequence:modified
      peptide

<400> SEQUENCE: 5

Xaa Val Asn Val Xaa
 1               5

<210> SEQ ID NO 6
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa at position 1 is Ac-Phe(CH2SO3H)
<221> NAME/KEY: MOD_RES
<222> LOCATION: (4)
<223> OTHER INFORMATION: Xaa at position 4 is Val-NH2
<223> OTHER INFORMATION: Description of Artificial Sequence:modified
      peptide

<400> SEQUENCE: 6

Xaa Val Asn Xaa
 1

<210> SEQ ID NO 7
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa at position 1 is Ac-Phe(CH2PO3H2)
<221> NAME/KEY: MOD_RES
<222> LOCATION: (4)
<223> OTHER INFORMATION: Xaa at position 4 is Val-NH2
<223> OTHER INFORMATION: Description of Artificial Sequence:modified
      peptide

<400> SEQUENCE: 7

Xaa Val Asn Xaa
 1

<210> SEQ ID NO 8
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa at position 1 is Ac-Tyr(PO3H2)
<221> NAME/KEY: MOD_RES
<222> LOCATION: (5)
<223> OTHER INFORMATION: Xaa at position 5 is Ser-NH2
<223> OTHER INFORMATION: Description of Artificial Sequence:modified
      peptide

<400> SEQUENCE: 8

Xaa Val Asn Val Xaa
 1               5

<210> SEQ ID NO 9
```

```
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa at position 1 is Ac-Tyr(PO3H2)
<221> NAME/KEY: MOD_RES
<222> LOCATION: (5)
<223> OTHER INFORMATION: Xaa at position 5 is Gln-NH2
<223> OTHER INFORMATION: Description of Artificial Sequence:modified
      peptide

<400> SEQUENCE: 9

Xaa Val Asn Val Xaa
 1               5

<210> SEQ ID NO 10
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa at position 1 is
      6-biotinamido-hexanoyl-Tyr(PO3H2)
<221> NAME/KEY: MOD_RES
<222> LOCATION: (4)
<223> OTHER INFORMATION: Xaa at position 4 is Val-NH2
<223> OTHER INFORMATION: Description of Artificial Sequence:modified
      peptide

<400> SEQUENCE: 10

Xaa Val Asn Xaa
 1

<210> SEQ ID NO 11
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa at position 1 is Ac-Tyr(PO3H2)
<221> NAME/KEY: MOD_RES
<222> LOCATION: (4)
<223> OTHER INFORMATION: Xaa at position 4 is Val-NH2
<223> OTHER INFORMATION: Description of Artificial Sequence:modified
      peptide

<400> SEQUENCE: 11

Xaa Val Asn Xaa
 1

<210> SEQ ID NO 12
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa at position 1 is Ac-Tyr(PO3HMe)
<221> NAME/KEY: MOD_RES
<222> LOCATION: (4)
<223> OTHER INFORMATION: Xaa at position 4 is Val-NH2
<223> OTHER INFORMATION: Description of Artificial Sequence:modified
      peptide

<400> SEQUENCE: 12

Xaa Val Asn Xaa
 1
```

```
<210> SEQ ID NO 13
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa at position 1 is Ac-Tyr(PO3Et2)
<221> NAME/KEY: MOD_RES
<222> LOCATION: (4)
<223> OTHER INFORMATION: Xaa at position 4 is Val-NH2
<223> OTHER INFORMATION: Description of Artificial Sequence:modified
      peptide

<400> SEQUENCE: 13

Xaa Val Asn Xaa
  1

<210> SEQ ID NO 14
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa at position 1 is Ac-Tyr(PO3H2)
<221> NAME/KEY: MOD_RES
<222> LOCATION: (5)
<223> OTHER INFORMATION: Xaa at position 5 is Ser-NH2
<223> OTHER INFORMATION: Description of Artificial Sequence:modified
      peptide

<400> SEQUENCE: 14

Xaa Ile Asn Gln Xaa
  1               5

<210> SEQ ID NO 15
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa at position 1 is Ac-Tyr(PO3H2)
<221> NAME/KEY: MOD_RES
<222> LOCATION: (5)
<223> OTHER INFORMATION: Xaa at position 5 is Glu-NH2
<223> OTHER INFORMATION: Description of Artificial Sequence:modified
      peptide

<400> SEQUENCE: 15

Xaa Val Asn Ile Xaa
  1               5

<210> SEQ ID NO 16
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa at position 1 is Ac-Tyr(PO3H2)
<221> NAME/KEY: MOD_RES
<222> LOCATION: (5)
<223> OTHER INFORMATION: Xaa at position 5 is Lys-NH2
<223> OTHER INFORMATION: Description of Artificial Sequence:modified
      peptide

<400> SEQUENCE: 16

Xaa Ile Asn Ile Xaa
  1               5
```

```
<210> SEQ ID NO 17
<211> LENGTH: 6
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa at position 1 is CH3-(CH2)12-CO-Gly
<221> NAME/KEY: MOD_RES
<222> LOCATION: (3)
<223> OTHER INFORMATION: Xaa at position 3 is Tyr(PO3H2)
<221> NAME/KEY: MOD_RES
<222> LOCATION: (6)
<223> OTHER INFORMATION: Xaa at position 6 is Val-NH2
<223> OTHER INFORMATION: Description of Artificial Sequence:modified
      peptide

<400> SEQUENCE: 17

Xaa Gly Xaa Val Asn Xaa
 1               5

<210> SEQ ID NO 18
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa at position 1 is CH3-(CH2)12-CO-Tyr(PO3H2)
<221> NAME/KEY: MOD_RES
<222> LOCATION: (4)
<223> OTHER INFORMATION: Xaa at position 4 is Val-NH2
<223> OTHER INFORMATION: Description of Artificial Sequence:modified
      peptide

<400> SEQUENCE: 18

Xaa Val Asn Xaa
 1

<210> SEQ ID NO 19
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa at position 1 is CH3-(CH2)12-CO-Tyr(PO3H2)
<221> NAME/KEY: MOD_RES
<222> LOCATION: (4)
<223> OTHER INFORMATION: Xaa at position 4 is Val-NH2
<223> OTHER INFORMATION: Description of Artificial Sequence:modified
      peptide

<400> SEQUENCE: 19

Xaa Val Asn Xaa
 1

<210> SEQ ID NO 20
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa at position 1 is C6H11-Ch2-CO-Tyr(PO3H2)
<221> NAME/KEY: MOD_RES
<222> LOCATION: (4)
<223> OTHER INFORMATION: Xaa at positon 4 is Val-NH2
<223> OTHER INFORMATION: Description of Artificial Sequence:modified
      peptide
```

-continued

```
<400> SEQUENCE: 20

Xaa Val Asn Xaa
 1

<210> SEQ ID NO 21
<211> LENGTH: 21
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa at position 1 is 6-biotinamido-hexanoyl-Gly
<221> NAME/KEY: MOD_RES
<222> LOCATION: (10)
<223> OTHER INFORMATION: Xaa at position 10 is Tyr(PO3H2)
<221> NAME/KEY: MOD_RES
<222> LOCATION: (17)
<223> OTHER INFORMATION: Xaa at position 17 is Tyr(PO3H2)
<221> NAME/KEY: MOD_RES
<222> LOCATION: (21)
<223> OTHER INFORMATION: Xaa at position 21 is Lys-OH
<223> OTHER INFORMATION: Description of Artificial Sequence:modified
      peptide

<400> SEQUENCE: 21

Xaa Gly Gly Gly Gly Ile Gly Gln His Xaa Val His Val Asn Ala Thr
 1               5                  10                  15

Xaa Val Asn Val Xaa
            20

<210> SEQ ID NO 22
<211> LENGTH: 21
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa at position 1 is 6-biotinamido-hexanoyl-Gly
<221> NAME/KEY: MOD_RES
<222> LOCATION: (17)
<223> OTHER INFORMATION: Xaa at position 17 is tyr(PO3H2)
<221> NAME/KEY: MOD_RES
<222> LOCATION: (21)
<223> OTHER INFORMATION: Xaa at position 21 is Lys-OH
<223> OTHER INFORMATION: Description of Artificial Sequence:modified
      peptide

<400> SEQUENCE: 22

Xaa Gly Gly Gly Gly Ile Gly Gln His Tyr Val His Val Asn Ala Thr
 1               5                  10                  15

Xaa Val Asn Val Xaa
            20

<210> SEQ ID NO 23
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa at position 1 is H-Tyr(PO3H2)
<221> NAME/KEY: MOD_RES
<222> LOCATION: (5)
<223> OTHER INFORMATION: Xaa at position 5 is Lys-OH
<223> OTHER INFORMATION: Description of Artificial Sequence:modified
      peptide

<400> SEQUENCE: 23

Xaa Val Asn Val Xaa
 1               5
```

```
<210> SEQ ID NO 24
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Xaa at position 1 is Ac-Phe
<221> NAME/KEY: MOD_RES
<222> LOCATION: (4)
<223> OTHER INFORMATION: Xaa at position 4 is Val-OH
<223> OTHER INFORMATION: Description of Artificial Sequence:modified
      peptide

<400> SEQUENCE: 24

Xaa Val Asn Xaa
```